US011452620B2

(12) United States Patent
Furore et al.

(10) Patent No.: US 11,452,620 B2
(45) Date of Patent: Sep. 27, 2022

(54) ACETABULAR LINER EXTRACTION

(71) Applicant: Zimmer, Inc., Warsaw, IN (US)

(72) Inventors: Adam Furore, Warsaw, IN (US);
Walter W. Thomas, Warsaw, IN (US);
Robert D. Krebs, Warsaw, IN (US);
Andrew Hartman, Warsaw, IN (US);
Jacob Macke, Warsaw, IN (US); Colin Eric Lasko, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 312 days.

(21) Appl. No.: 16/448,623

(22) Filed: Jun. 21, 2019

(65) Prior Publication Data

US 2019/0388243 A1 Dec. 26, 2019

Related U.S. Application Data

(60) Provisional application No. 62/688,839, filed on Jun. 22, 2018.

(51) Int. Cl.
*A61F 2/34* (2006.01)
*A61F 2/46* (2006.01)
*A61F 2/30* (2006.01)

(52) U.S. Cl.
CPC .............. *A61F 2/4637* (2013.01); *A61F 2/34* (2013.01); *A61F 2/4609* (2013.01); *A61F 2/4603* (2013.01); *A61F 2002/3069* (2013.01); *A61F 2002/3093* (2013.01); *A61F 2002/4619* (2013.01); *A61F 2002/4641* (2013.01); *A61F 2002/4681* (2013.01)

(58) Field of Classification Search
CPC .... A61F 2/4603; A61F 2/4609; A61F 2/4637; A61F 2002/4641; A61F 2002/4681; A61F 2/34; A61F 2002/4619
See application file for complete search history.

(56) References Cited

U.S. PATENT DOCUMENTS

| 6,022,357 | A | 2/2000 | Reu et al. |
| 2003/0187512 | A1 | 10/2003 | Frederick et al. |
| 2007/0005144 | A1 | 1/2007 | Leisinger et al. |
| 2014/0228854 | A1 | 8/2014 | Witt et al. |
| 2015/0250614 | A1* | 9/2015 | Davenport ............ A61F 2/4609 606/99 |

FOREIGN PATENT DOCUMENTS

| CN | 112334094 A | 2/2021 |
| WO | WO-2019246523 A1 | 12/2019 |

OTHER PUBLICATIONS

"International Application Serial No. PCT/US2019/038474, International Preliminary Report on Patentability dated Dec. 30, 2020", 9 pgs.

(Continued)

*Primary Examiner* — Christopher D. Prone
(74) *Attorney, Agent, or Firm* — Schwegman Lundberg & Woessner, P.A.

(57) ABSTRACT

A tool assembly for extracting a liner from a prosthesis comprising an impactor and a faceplate. The impactor can be configured to receive and transmit a force. The faceplate can be configured to deliver the force from the impactor to the prosthesis to separate the liner from a shell of the prosthesis.

20 Claims, 18 Drawing Sheets

(56) References Cited

OTHER PUBLICATIONS

"International Application Serial No. PCT US2019 038474, International Search Report dated Sep. 30, 2019", 4 pgs.
"International Application Serial No. PCT US2019 038474, Written Opinion dated Sep. 30, 2019", 7 pgs.
"European Application Serial No. 19745341.8, Response to Communication pursuant to Rules 161(1) and 162 EPC filed Aug. 13, 2021", 18 pgs.

\* cited by examiner

ACETABULAR LINER EXTRACTION

CLAIM OF PRIORITY

This patent application claims the benefit of priority, under 35 U.S.C. Section 119(e), to Jacob Macke, U.S. Patent Application Ser. No. 62/688,839, entitled "ACETABULAR LINER EXTRACTION," filed on Jun. 22, 2018, which is hereby incorporated by reference herein in its entirety.

BACKGROUND

During a hip arthroplasty, an outer shell can be secured to an acetabulum of a hip of a patient where the outer shell is configured to promote bony ingrowth to obtain a strong connection between the prosthesis in the hip. Often, a liner is secured to a concave inner side of the shell to provide a smooth and resilient articulation surface for interaction with a femoral head or a femoral implant. In some cases, the liner must be removed during a revision procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
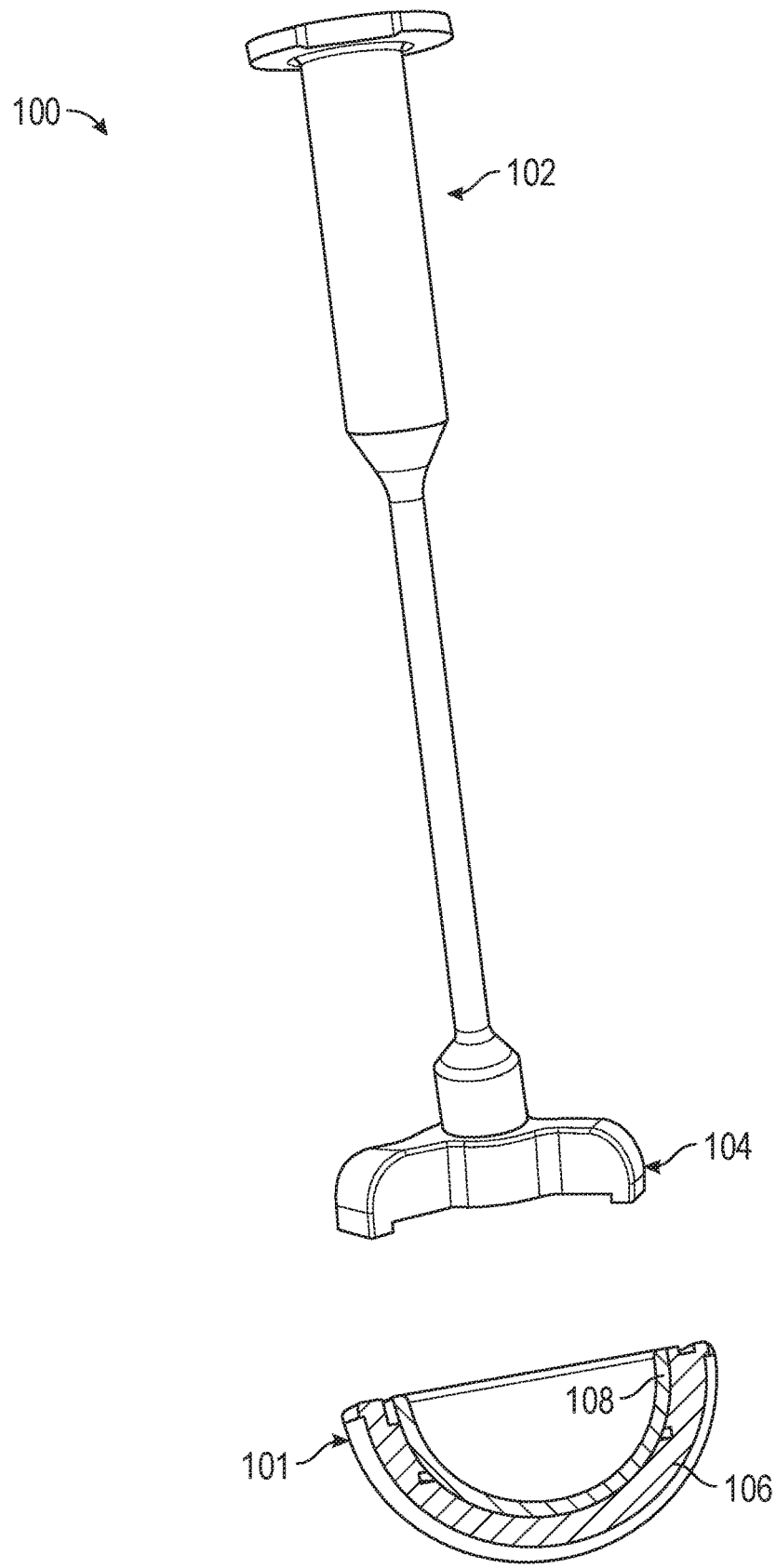
FIG. 1 illustrates an isometric view of a tool assembly, in accordance with at least one example of this disclosure.

Hard bearing liners (such as ceramic or metal) can be difficult to remove from acetabular shells during revisions. If unsuccessful, the surgeon may need to remove the liner in pieces, which can be time consuming. Alternatively, the surgeon may be required to remove the entire liner and shell assembly, resulting in additional bone loss and longer healing times.

The inventors have developed tool assemblies to address the problem of removing a liner from an outer shell. In one example, the tool can include a handle that is securable to a faceplate configured to engage an outer edge or lip of the shell. The handle can be impacted to transmit a force to the shell to In one example, after dislocating a hip, an acetabular liner can be lavaged and dried. An adhesive or bonding material (e.g., resin composite filling, or the like) can be applied to an apex of the liner. An extraction device can be placed around an outer rim of a shell. A T-handle with specific distal geometry can be fed through a center of the faceplate extractor until contact is made with the bonding agent. The adhesive material can dry, polymerize, or be cured utilizing UV light, or the like. Once cured, the T-handle can be rotated counterclockwise upon which an axial force will be applied to the apex of the liner releasing it from the shell.

Currently, some acetabular constructs are implanted with a dual-mobility Cobalt Chromium (CoCr) liner, which can be difficult to revise. Due to the thin cross-section of the liner, the liner can have a particularly strong taper connection with the shell. This becomes further amplified in vivo when a galvanic couple between CoCr and titanium 6 aluminum 14 vanadium (Ti6Al4V) begins to corrode slightly, further securing the liner and the shell. This creates the need for a tool to remove the dual-mobility liner from this construct without disturbing the shell-bone interface.

Currently, when a dual-mobility liner cannot be removed by disturbing the taper connection with vibration, surgeons often turn to burring and cutting the liner which can generate large amounts of metal debris (such as sparks and/or dust). The proposed solutions instead can create metal shavings which can be contained within the liner, and removed using vacuum. Further, the proposed solutions can help minimize risk of disturbing the shell-bone interface.

In another examples, a jig or faceplate, which can interface with a rim of the shell, can be placed against a shell. A sleeve can be secured to the faceplate and bushings can be used to guide a drill and tap, which can be used to create a threaded bore in the apex of the metal liner. The bushing can be removed from the threaded hole and the bore can be engaged by an extraction device (or handle). A shoulder bolt can pass through the extraction device and can engage the threaded bore of the liner. Torque can be applied to the extraction device to distract the shoulder bolt, and in turn, the liner. This axial force is countered by an equal and opposite axial force against the shell, effectively applying no force to the bone-shell interface. This device allows for a large amount of torque to be applied to the liner, allowing for liner removal in most cases, regardless of its corroded state. Certain design iterations can accommodate all shell sizes using a variety of faceplates of different sizes and shapes. The same extraction device could mate with another device which is attached to the liner using bone cement or another biocompatible adhesive. In another example, a threaded hole can be created during initial manufacture of the shell.

Another proposed solution discussed herein crushes the liner without generating any metal (CoCr) debris. Further, this solution can help to minimize risk of disturbing the shell-bone interface.

In another example, a device can engage with "scallops" between the CoCr liner and the shell. The device can apply inward lateral pressure to crush the liner in a clover-like shape around a disc or ball. The crushing action can be mechanically advantaged using either levers, linkages, gears, and may include power actuation. Once the liner is crushed, it can be extracted from the shell by opposing force on the shell, so as to not disrupt the shell-bone interface. The liner can then be discarded.

The above discussion is intended to provide an overview of subject matter of the present patent application. It is not intended to provide an exclusive or exhaustive explanation of the invention. The description below is included to provide further information about the present patent application.

FIG. 1 illustrates an isometric view of a tool assembly 100, in accordance with at least one example of this disclosure. The tool assembly 100 can be configured to engage a prosthesis to deliver a force thereto for separation of a liner of the prosthesis from a shell of the prosthesis, which can be particularly helpful during hip arthroplasty revision procedures. Further details of the tool assembly 100 are discussed below.

The tool assembly 100 can include an impactor 102 and a faceplate 104. Also shown in FIG. 1 is a prosthesis 101 (or an implant 101). The implant 101 can include an outer shell 106 and a liner 108.

Each of the components of the tool assembly 100 can be comprised of materials such as one or more of metals, plastics, foams, elastomers, ceramics, composites, combinations thereof, or the like. The impactor 102 can be an elongate impactor configured for insertion into a cavity of a patient and can include a coupler releasably securable to the faceplate 104. The faceplate 104 can be configured to engage the outer shell 106 of the implant and can be configured to receive a force from the impactor and can be configured to transmit the force to the implant 101 (namely, the outer shell 106).

The implant 101 can be a prosthesis configured for insertion into a human body for a full or partial arthroplasty. For example, the implant can be configured to be inserted into a glenoid for a shoulder arthroplasty or an acetabulum for a hip arthroplasty. The components of the implant 101 can be made of solid biocompatible materials such as stainless steels, cobalt chromium, titanium, combinations thereof, or the like. In some examples, the implant 101 can be made of porous or semi-porous materials configured to promote bone ingrowth to enhance fixation (such as through osseointegration). For example, the outer shell 106 can be made of a semi-porous material and the liner 108 can be made of a solid and smooth material. One porous material that can be used for the shell 106 is OsseoTi™ porous metal from Zimmer Biomet™ (Warsaw, Ind.). OsseoTi can be made of Ti6Al4V and can have a porous structure that generally mimics a porous structure of human cancellous bone. Also, the porous material can be Trabecular Metal™, also from Zimmer Biomet. Also, the porous material can be Regenerex®, also from Zimmer Biomet. In other examples, other porous materials can be used. The liner can be made of rigid and solid materials, such as ceramics, CoCr, or the like.

In some examples, a revision procedure may need to be performed where the implant 101 is secured to a patient, such as in an acetabulum. In such a case, it may be desirable to remove the liner 108 from the shell 106, while minimizing disruption of osseointegration of the shell 106 and the acetabulum of the patient. That is, it may be desirable to not damage bone that is ingrown into the shell 106 during removal of the liner 108. The tool assembly can provide to remove the liner 108 while helping to limit disruption to the ingrown bone.

In such a procedure, an opening through tissue of the patient can be created, and the femur (and femoral implant, if present) can be separated from the implant 101. The faceplate 104 can be inserted into the opening to engage the outer shell 106 and the impactor 102 can be secured to the faceplate through a coupling interface. A force can then be applied to the impactor 102, such as through the use of a mallet or hammer. The impactor 102 can deliver the force to the faceplate 104, which can transfer the force to the shell 106. Vibrations in the shell 106 caused by the received force can cause the liner 108 to separate from the shell 106. The faceplate 104 can then be removed from the opening along with the impactor 102 and the revision or procedure can be completed. Further details and benefits of the tool assembly and various related embodiments are discussed in the FIGS. below.

Figure 2A:
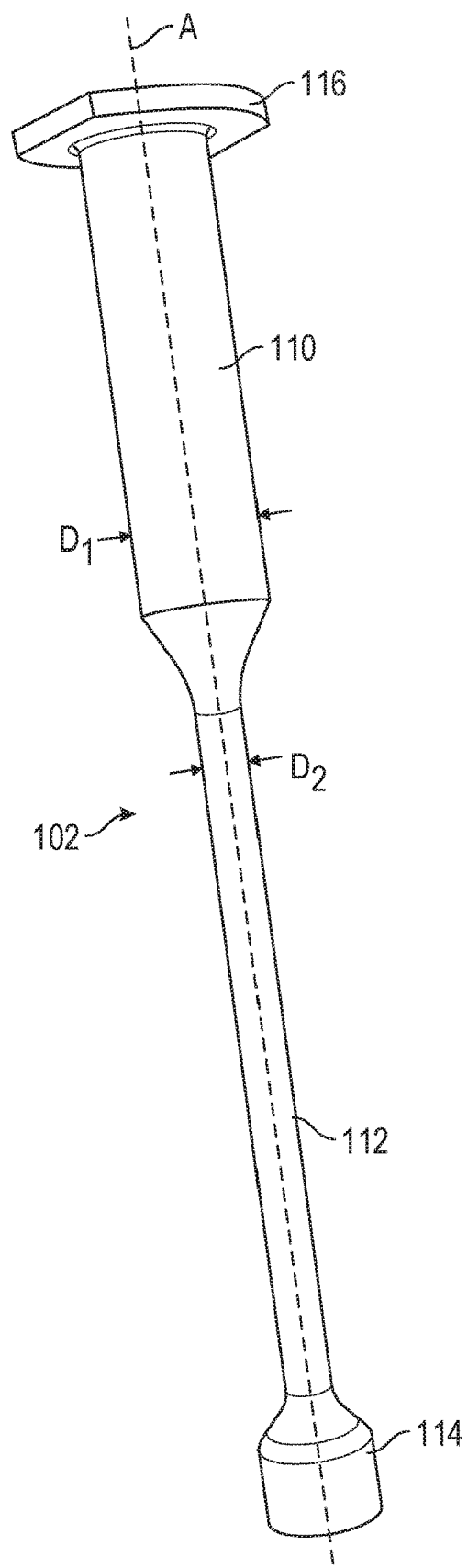
FIG. 2A illustrates an isometric view of an impactor of a tool assembly, in accordance with at least one example of this disclosure.
Figure 2B:
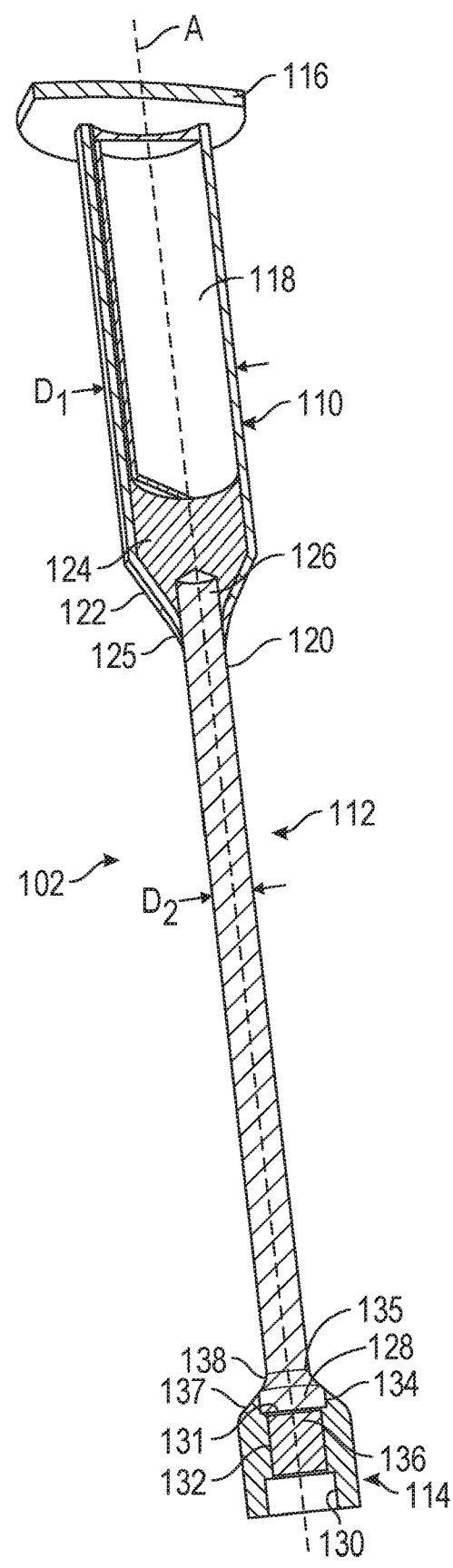
FIG. 2B illustrates a cross-sectional view of an impactor of a tool assembly, in accordance with at least one example of this disclosure.

FIG. 2A illustrates an isometric view of the impactor 102, in accordance with at least one example of this disclosure. FIG. 2B illustrates a cross-sectional view of the impactor 102, in accordance with at least one example of this disclosure. FIGS. 2A and 2B are discussed below concurrently. FIGS. 2A and 2B show orientation indicators Proximal and Distal, axis A, diameter D1, and diameter D2.

The impactor 102 of FIGS. 2A and 2B can be consistent with the impactor 102 of FIG. 1; further details of the impactor 102 are discussed below. For example, FIG. 2A shows that the impactor 102 can include a handle 110, a shaft 112, a coupler 114, and a strike plate 116.

The handle 110 can be can be a rigid or semi-rigid body extending proximally-to-distally along the axis A. The handle 110 can be sized and shaped to be grasped and operated. The handle 110 can be coupled to the shaft 112 at a distal portion of the handle 110, as described below in further detail.

The shaft 112 can be a rigid or semi-rigid and elongate body extending proximally-to-distally along the axis A. The shaft 112 can connect to the coupler 114 at a distal portion of the shaft 112. The coupler 114 can be a rigid or semi-rigid member configured to releasably secure a boss of the faceplate 104, as discussed in further detail below. The strike plate 116 can be a plate, disc, or other member having a relatively small thickness relative to its length, width, or radius. The strike plate 116 can be connected to a proximal portion of the handle 110 and can extend radially outward therefrom, and can also act as a proximal hand-stop.

FIG. 2B shows further details of each of the handle 110, the shaft 112, and the coupler 116. For example, FIG. 2B shows that the handle 102 can include a balance bore 118, a handle bore 120, a taper 122, and a solid portion 124 (or handle stop 124). The shaft 112 can include a proximal portion 126, the diameter D2, and a distal portion 128. The coupler 114 can include a coupler bore 130, a magnet bore 132, a shaft bore 134, a magnet 136, and a taper 138. The coupler bore 130, the magnet bore 132, and the magnet 136 can be referred to as a mating interface.

The balance bore 118 can be a bore extending along the axis A within the handle 110. The balance bore 118 can be sized to position a center of gravity of the impactor distal of the handle. That is, the balance bore can be sized to move the center of gravity of the impactor 102 distally, such that the impactor is easier to maneuver. The handle bore 120 can extend proximally into the handle 110 from a distal portion or end of the handle 110 and can terminate within a solid portion 124 of the handle (prior to intersecting the balance bore 118). The handle bore 120 can be sized and shaped to receive a proximal portion 126 of the shaft therein, such that the proximal portion 126 engages the solid portion 124 of the handle 110 when the shaft 112 is fully inserted into the handle bore 120. The handle stop (or solid portion) 124 can be configured to engage the proximal portion 126 of the shaft 112 within the handle bore 120, such that force is transmitted from the handle stop 124 to the shaft from to reduce fatigue on a weld 125 between the handle 110 and the shaft 112.

The taper 122 can taper from a diameter D1 of the handle 110 down to a diameter D2 of the shaft 112. In some examples, the handle 110 can be welded to the shaft 112 where the taper 122 meets the shaft 112 to help secure the handle 110 to the shaft. The diameter D2 can be sized to minimize loss of force transmission from the handle 110 to the coupler 114 during operation of the impactor 102. In some examples, the shaft 112 can be a solid piece to help avoid transmission loss through vibration and deformation of the shaft 112, especially during transfer of forces from the strike plate 116 to the coupler 114.

The coupler bore 130 can be located distally of the magnet bore 132. The coupler bore can be sized and shaped to receive a boss of the faceplate 104. The coupler bore 130 can be shaped to help limit rotation of the faceplate 104 with respect to the coupler 116. The coupler bore 130 can be square in some examples. In other examples, the coupler bore 130 can be hexolubular, triangular, hexagonal, rectangular, or the like.

The magnet bore 132 can be located proximally of the coupler bore 130 and distally of the shaft bore 134. The magnet bore 132 can be sized and shaped to support the magnet 136 therein. The magnet bore 132 can have a diameter smaller than the coupler bore 130 to limit proximal movement of the boss of the faceplate 104 with respect to the coupler 116. In some examples, the magnet 136 can have a length that is smaller than the magnet bore 132 to limit contact between the magnet 136 and the shaft 112 and to limit contact between the magnet 136 and a boss of the faceplate 104.

The shaft bore 134 can extend distally into the coupler 114 from a proximal portion 137 of the coupler 114. The shaft bore 134 can be sized and shaped to receive the shaft 112, such that the distal portion 128 extends into the shaft bore 134 to secure the shaft 112 to the coupler 114. In some examples, the coupler bore 130 can be adjacent to the magnet bore 132. In such a case, the distal portion 128 (and the coupler bore 130) can have a diameter larger than the magnet bore 132, to help limit translation of the distal portion 128 into the magnet bore 132. The coupler bore 130 can include a coupler stop 131 (which can be the radial face formed by the coupler bore 130 and the magnet bore 132), where the coupler stop 131 can engage the shaft 112 within the coupler bore 130 to transmit force from the shaft 112 to the coupler 114 through the coupler stop 131 to reduce fatigue on a weld 135 between the coupler 114 and the shaft 112.

The magnet 136 can be a permanent or electromagnet securable within the magnet bore 132. In some examples, the magnet 136 can be replaceable. The taper 138 can be a proximal outer portion of the coupler 116 configured to taper from a diameter of the coupler to a diameter of the shaft 112. In some examples, the shaft 112 can be welded to the coupler 116 at the taper 138 to help secure the coupler 116 to the shaft 112.

Further details of operation of the impactor is discussed below with respect to FIGS. 3A and 3B.

Figure 3A:
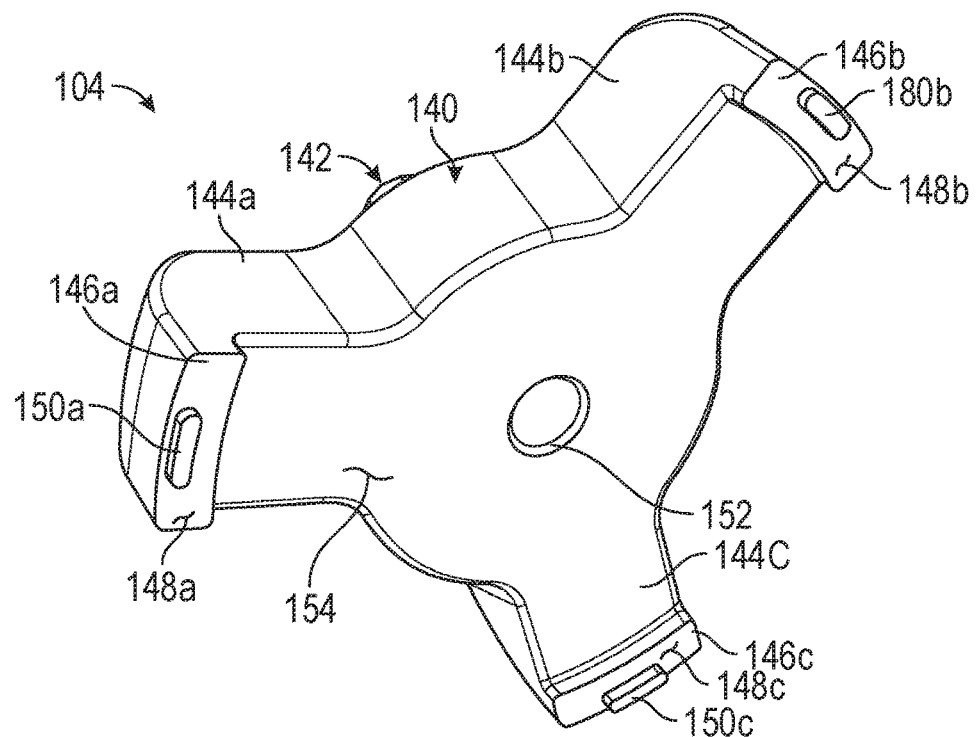
FIG. 3A illustrates an isometric view of a faceplate of a tool assembly, in accordance with at least one example of this disclosure.
Figure 3B:
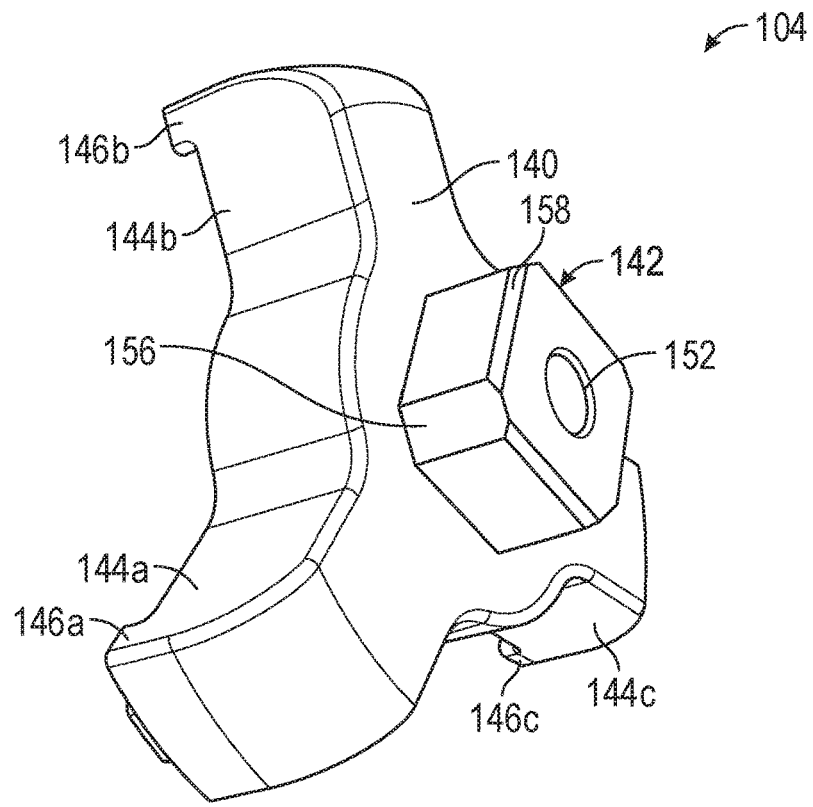
FIG. 3B illustrates an isometric view of a faceplate of a tool assembly, in accordance with at least one example of this disclosure.

FIG. 3A illustrates an isometric view of the faceplate 104 of the tool assembly, in accordance with at least one example of this disclosure. FIG. 3B illustrates an isometric view of the faceplate 104 of the tool assembly, in accordance with at least one example of this disclosure. FIGS. 3A and 3B are discussed below concurrently. The faceplate 104 can be consistent with FIG. 1 above; further details of the faceplate are discussed below.

For example, the faceplate 104 can include a body 140, a boss 142, and arms 144a-144c (collectively referred to as the arms 144). The arms 144a-144c can respectively include extensions 144a-144c. The extensions 146a-146c can respectively include distal surfaces 148a-148c and feet 150a-150c. The body 140 can include a central bore 152 and a distal surface 154. The boss 142 can include chamfers 156 and chamfers 158. FIGS. 3A and 3B also show orientation indicators Proximal and Distal.

The body 140 can be a rigid or semi-rigid member having a substantially circular or cylindrical shape. The body can have other shapes in other examples such as a triangular prism, a rectangular prism, a hexagonal prism, or the like. The body 140 can be solid in some examples and can be hollow in other examples. The body 140 can support the boss 142 such that the boss 142 extends proximally from a proximal surface or portion of the body 140.

The boss 142 can be a rigid projection extending from the body 140 and can have a substantially rectangular prism shape. The boss 142 can have other shapes in other examples, such as a triangular prism, a hexagonal prism, a hexolubular prism, or the like. As discussed above, the coupler bore 130 can have a substantially rectangular shape, where the coupler bore 130 is complimentary to the substantially rectangular prism shape of the boss 142. The boss 142 can be made of a material that is magnetizable (or reactive to the magnet 136). For example, the boss 142 can be made of one or more of iron, nickel, cobalt, rare-earth metals alloys, steel alloys, or the like. The boss 142 can include chamfers 156 and chamfers 158 which can reduce friction between the boss 142 and the coupler 114 during insertion of the boss 142 into the coupler 114, which can save time during a procedure and can reduce wear on the boss 142.

The arms 144a-144c can each connect to the body and can extend radially outward from the body 140 such that the arms 144 are substantially evenly spaced. Though 3 of the arms 144 are shown, 2, 3, 5, 6, 7, 8, 9, 10, or the like arms can be connected to the body 140. In some examples, the arms 144 can be unevenly spaced. The extensions 146a-146c can extend distally from respective arms 144a-144c and can each define respective distal surfaces 148a-148c at distal portions of the extensions 146a-146c. The distal surfaces (or faces) 148 can be configured to contact the outer shell of the implant and can be configured to deliver force from the body 140 to the outer shell 106.

The feet 150a-150c can respectfully extend distally from the distal surfaces 148a-148c. Each of the feet 150 can be insertable into a notch of the outer shell 106 to limit rotation of the faceplate 114 with respect to the outer shell 106 when the feet 150 are positioned within the notch.

In some examples, the tool assembly 100 can include a plurality of faceplates sized to engage implants of various sizes. In such an example, each faceplate can have arms and/or extensions and/or bodies of various sizes while the boss of each faceplate can be substantially the same size, allowing the impactor 102 to be used with faceplates of various sizes for removal of implants of various sizes.

The central bore 152 can extend through the body 140 and the boss 142. The central bore 152 can be sized to receive tools (such as a tap, drill, or the like) therethrough for engagement of the tools with the liner 108 while the faceplate 104 engages the outer shell 106. The distal surface 154 can be located proximally of the distal surfaces 148 of the extensions, which can allow the liner 108 to be received within the extensions 146 during extraction of the liner 108.

In operation of some examples, an opening through tissue of the patient can be created, and the femur (and femoral implant, if present) can be separated from the implant 101, as discussed above. The faceplate 104 can be inserted into the opening such that the extensions 146 engage the outer shell 106. The faceplate 104 can be rotated with respect to the implant to allow the feet 150 to be inserted into notches of the outer shell 106 to limit rotation of the faceplate 104 with respect to the outer shell 106.

The faceplate 104 can be secured to the coupler 116 by inserting the boss 142 into the coupler bore 130 (shown in FIG. 2B). During insertion of the boss 142, the magnet 136 can attract the boss 142 to draw into the coupler bore 130 and to help retain the boss 142 within the coupler bore 130 to secure the impactor 102 to the faceplate 104. A force can then be applied to the strike plate 116 of the impactor 102, such as through the use of a mallet or hammer. The impactor 102 can deliver force through the handle 110, through the shaft 112, through the coupler 114, through the boss 142, to the arms 144, to the extensions 146, and to the outer the shell 106 through contact between the outer shell 106 and the distal surfaces 148 and the feet 150. Vibrations in the shell 106 caused by the received force can cause the liner 108 to separate from the shell 106. The recess between the distal surfaces 148 and the distal surface 154 of the body 140 can allow the liner 106 to move proximally 106. The faceplate 104 can then be removed from the opening along with the impactor 102 so that the liner 108 can be removed from the shell 106 and the revision or procedure can be completed. Such a procedure allows for the liner 108 to be removed while limiting creation of debris within the opening or cavity of the patient.

Figure 4A:
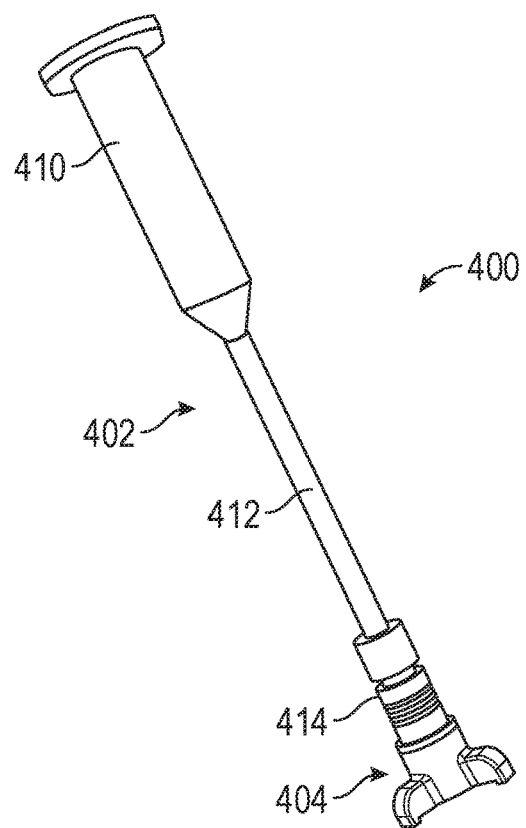
FIG. 4A illustrates an isometric view of a tool assembly, in accordance with at least one example of this disclosure.
Figure 4B:
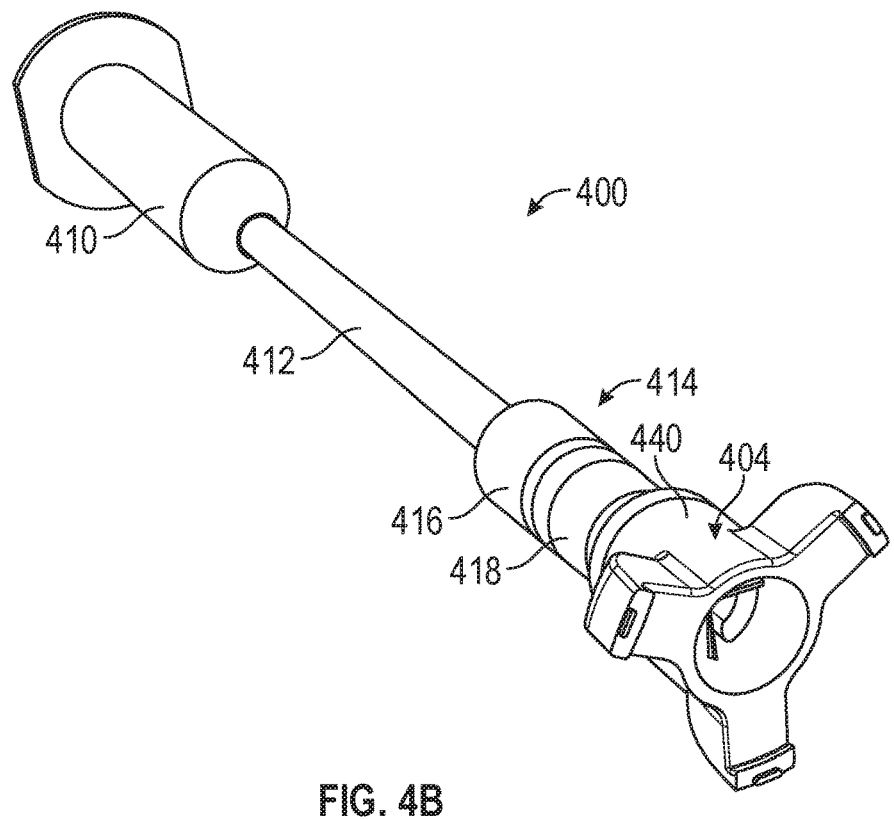
FIG. 4B illustrates an isometric view of a tool assembly, in accordance with at least one example of this disclosure.

FIG. 4A illustrates an isometric view of a tool assembly 400, in accordance with at least one example of this disclosure. FIG. 4B illustrates an isometric view of the tool assembly 400, in accordance with at least one example of this disclosure. The tool assembly 400 can be similar to the tool assembly 100 discussed above with respect to FIGS. 1-3B, except that the tool assembly 400 can include a coupler having a collar and a stem. Any of the previous or later discussed tool assemblies can be modified to include such a coupler.

The tool assembly 400 can include a faceplate 404, a handle 410, a shaft 412, and a coupler 414, which can include a collar 416 and a stem 418. FIGS. 4A and 4B also show orientation indicators Proximal and Distal.

The collar 416 can be connected to the shaft 412 near a distal end of the shaft. The collar 416 can be translatable with respect to the shaft 412. The stem 418 can be connected to a body 440 of the faceplate 404 and the stem 418 can extend proximally from the body 440. The stem 418 can be insertable into the collar 416 to secure the shaft 412 to the faceplate 414. The collar 416 can be translatable along the shaft 412 to release the collar 416 from the stem 418 and to release the faceplate 404 from the shaft 412.

Figure 5:
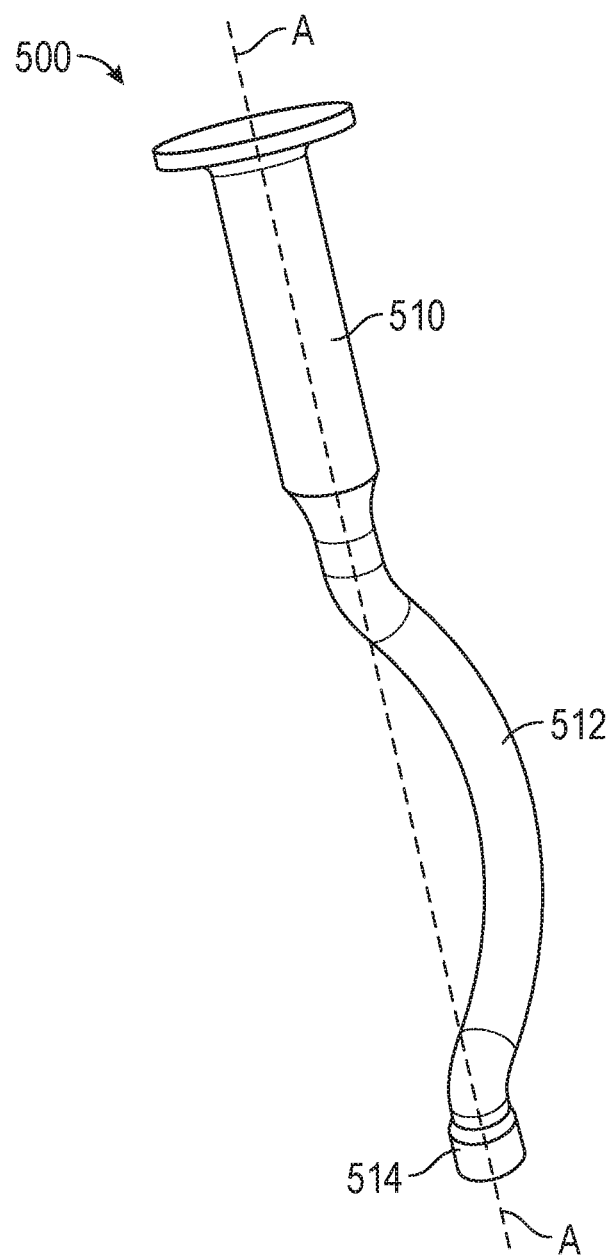
FIG. 5 illustrates an isometric view of a tool assembly, in accordance with at least one example of this disclosure.

FIG. 5 illustrates an isometric view of a tool assembly 500, in accordance with at least one example of this disclosure. The tool assembly 500 can have a shaft that is curved relative to a longitudinal axis of its handle and coupler. Any of the previous or later discussed tool assemblies can have such a shaft.

The tool assembly 500 can include a handle 510, a shaft 512, and a coupler 514. FIG. 5 also shows orientation indicators Proximal and Distal and axis A. The tool assembly 500 can be similar to the tool assemblies discussed above with respect to FIGS. 1-4A; however, the tool assembly 500 can include the shaft 512, that can be curved with respect to the axis A where the handle 510 and the coupler 514 can be coaxial with the axis A. Such a curved shaft can allow for a surgeon or physician to impact a faceplate around bones or tissue of the patient, which can be useful for an anterior revision approach.

Figure 6A:
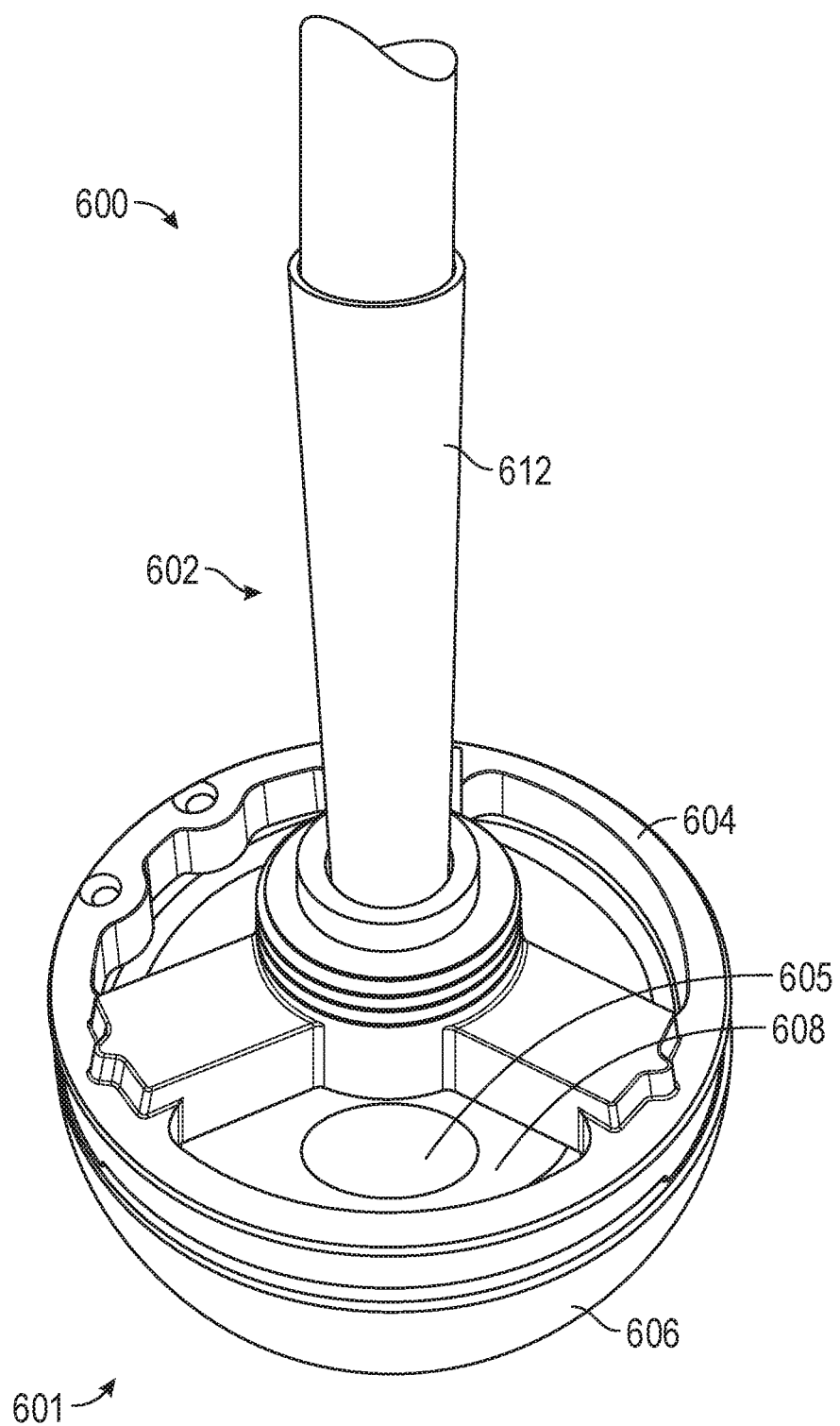
FIG. 6A illustrates an isometric view of a tool assembly, in accordance with at least one example of this disclosure.
Figure 6B:
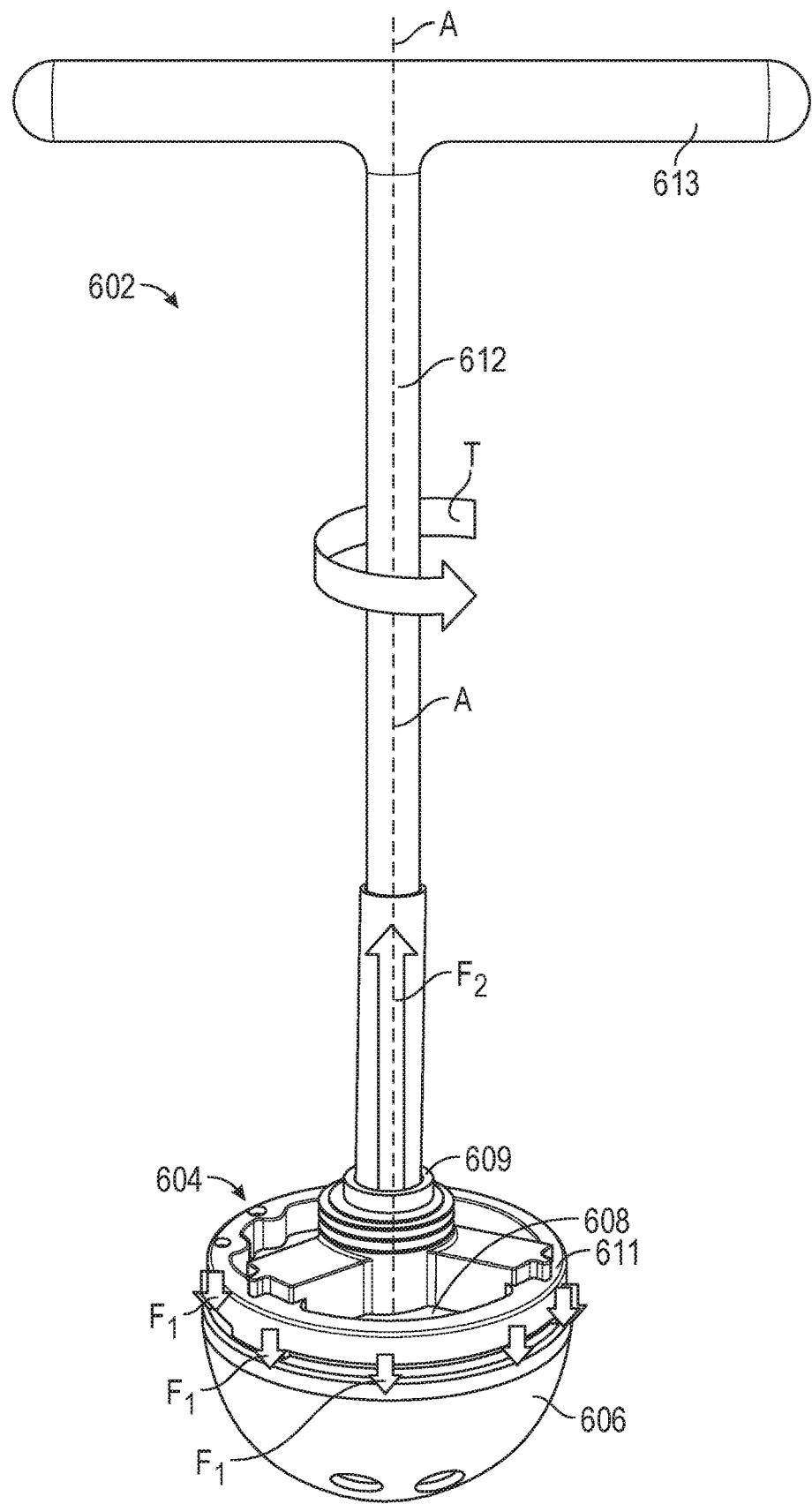
FIG. 6B illustrates an isometric view of a tool assembly, in accordance with at least one example of this disclosure.

FIG. 6A illustrates an isometric view of a tool assembly 600, in accordance with at least one example of this disclosure. FIG. 6B illustrates an isometric view of a tool assembly 600, in accordance with at least one example of this disclosure. FIGS. 6A and 6B are discussed below concurrently.

The tool assembly 600 can include a removal tool 602 and a faceplate 604. An implant 601 can include an outer shell 606 and a liner 608. The faceplate 604 can include a bore 609 (such as a central bore) and an outer ring 611. The removal tool 602 can include a shaft 612 and a handle 613. Also shown in FIG. 6A is an adhesive 605 and orientation indicators Proximal and Distal. Also shown in FIG. 6B are axis A, Forces F1, Force F2, and torque T.

The outer ring 611 of the faceplate 604 can be configured to engage the shell 606 and can include arms connecting the outer ring 611 to a collar including the bore 609 where the bore is configured to receive the shaft 609 therein for coupling the shaft 612 to the faceplate, such as through a threaded engagement.

The shaft 612 can extend substantially along the axis A and the handle 613 can be connected to a proximal portion of the shaft 612. A distal portion of the shaft 612 can be configured for insertion into the liner 606 and to be secured to the liner 606 using the adhesive 605. The adhesive 605 can be a resin, composite filling, or the like.

In operation of some examples, the liner 606 can be lavaged and dried. The faceplate 604 can be secured to the shell 606. Either before or after securing the faceplate, the adhesive 605 can be applied to a nadir or low point (apex from an inverted perspective) of the liner 606. The shaft 612 can be inserted into the bore 609 and secured to the faceplate 604 and can be positioned to contact the adhesive 605.

The adhesive 605 can then be cured or allowed to set to secure the shaft 612 of the removal tool 602 to the liner 608. The handle 613 of the removal tool 602 can be rotated to apply the torque T to the shaft 612, causing the faceplate 604 to create the forces F1 applied to the shell 606 and causing the shaft 612 to apply the force F2 to the liner 608 through the adhesive 605. The force F2 can cause shaft 612 to separate the liner 608 from the shell 606 of the implant 601.

Figure 7:
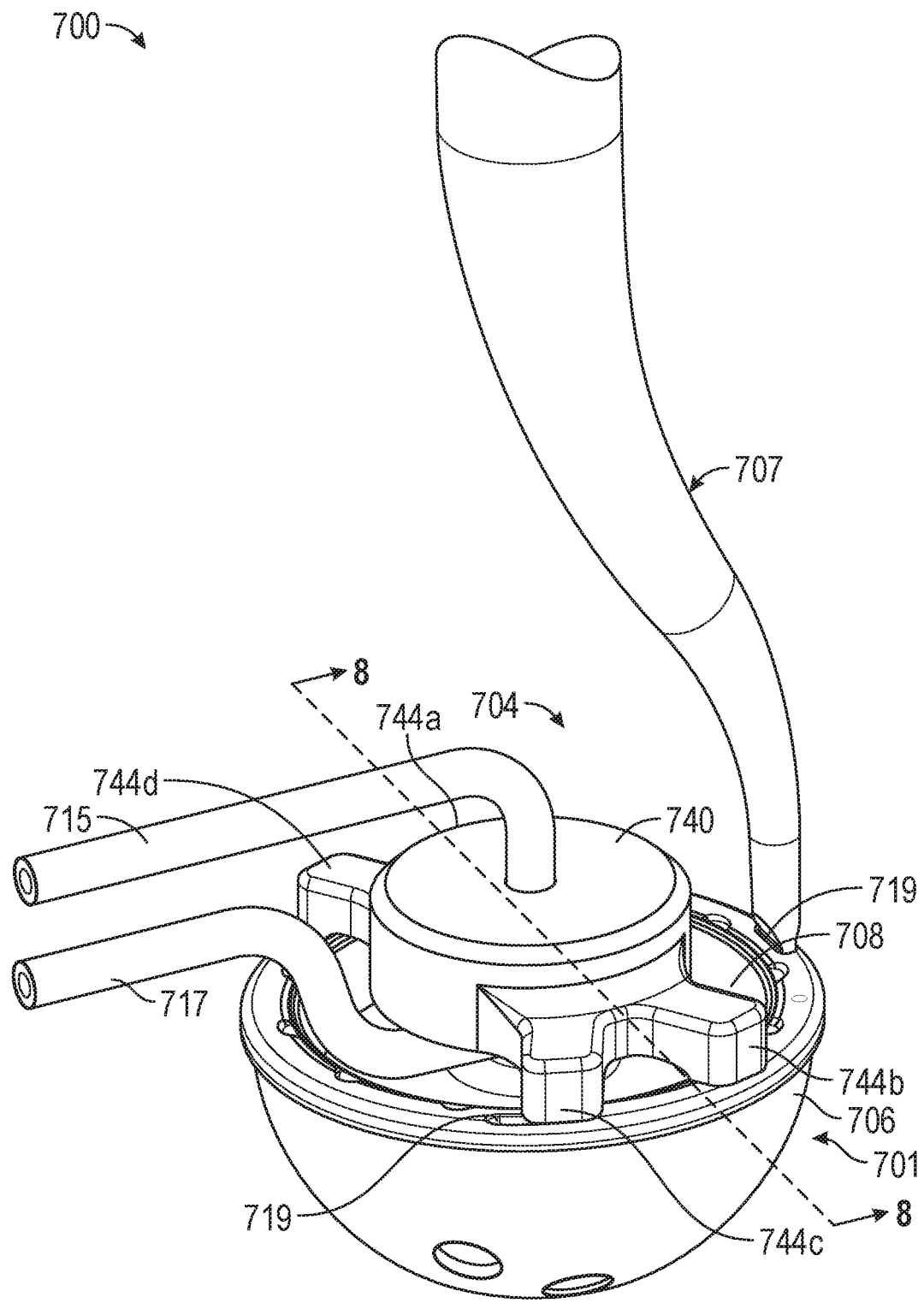
FIG. 7 illustrates an isometric view of a tool assembly, in accordance with at least one example of this disclosure.

FIG. 7 illustrates an isometric view of a tool assembly 700, in accordance with at least one example of this disclosure. The tool assembly 700 can include a suction and plunger system for assisting in removal of a liner from a shell of an implant. Any of the previously or later discussed tool assemblies can include such components.

The tool assembly 700 can include a faceplate 704, a tamp 707, and suction conduits 715 and 717. The faceplate 704 can include a body 740 and arms 744a-744d. An implant 701 can include an outer shell 706 and a liner 708. The outer shell 706 can include notches 719. Also shown in FIG. 7 are cross-sectional indicators 8-8 and orientation indicators Proximal and Distal.

The implant or prosthesis 701 can be similar to those discussed above, such that the liner 708 can be located within the outer shell 706 and secured thereto through an interference fit. The outer shell 706 can also include the notches 719 extending distally from a proximal face of the shell. The notches 719 can be configured to receive feet of the arms 744 and can be configured to receive the tamp 707 therein.

The tamp 707 can be an elongate tool, similar to an impactor, configured to deliver a force to the shell 706 through an opening of a patient. In some examples, the tamp 707 can be curved and in some examples, the tamp 707 can be substantially straight.

The suction conduits 715 and 717 can be tubes, pipes, or conduits configured to transmit fluids (such as air or other gasses) therethrough. The suction conduit 715 can be connected to a port in the body 740 and the suction conduit 717 can be connected to a port of a plunger of the body 740 (as discussed further below). Each of the suction conduits 715 and 717 can be connected to a vacuum or suction system of an operating room for applying suction to the components of the faceplate 704 for helping to remove the liner 708 from the shell 706.

As with other embodiments discussed above, the arms 744a-744d can connect to the body 740 and can extend radially outward therefrom. The arms 744 can be configured to engage the rim of the shell 706 and feet of the arms 744 can be configured to insert into the notches 719. Further details and operation of the tool assembly 700 are discussed below with respect to FIGS. 8A-9.

Figure 8A:
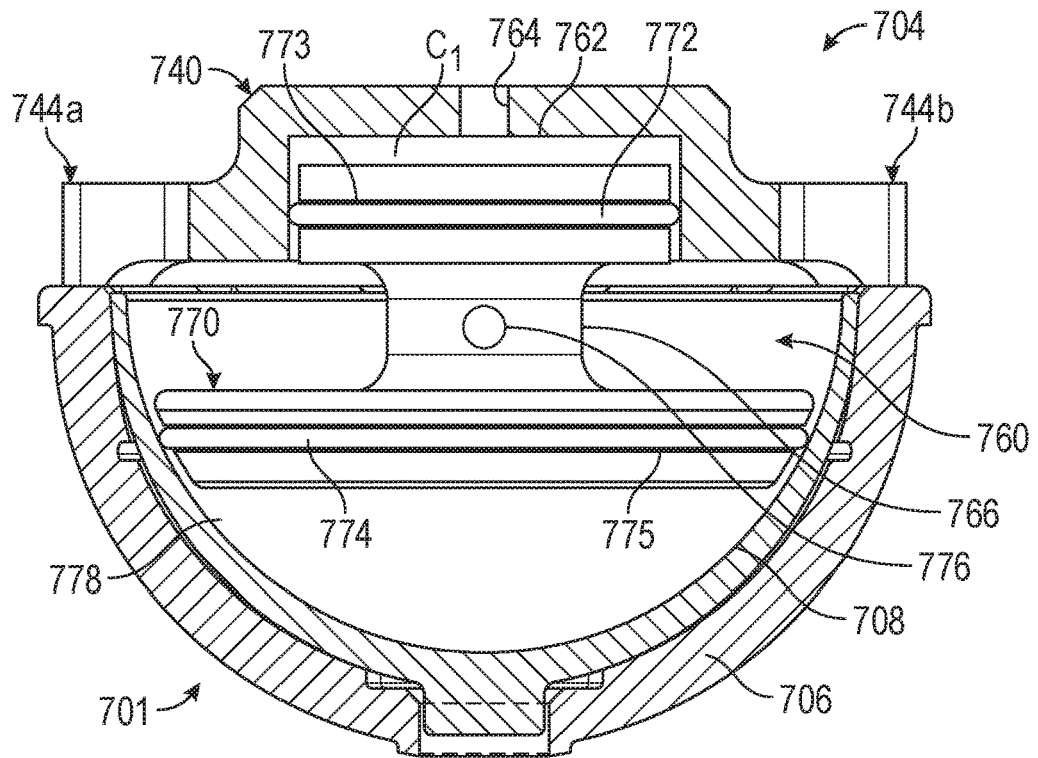
FIG. 8A illustrates a cross-sectional view of a portion of a tool assembly in a first condition, in accordance with at least one example of this disclosure.
Figure 8B:
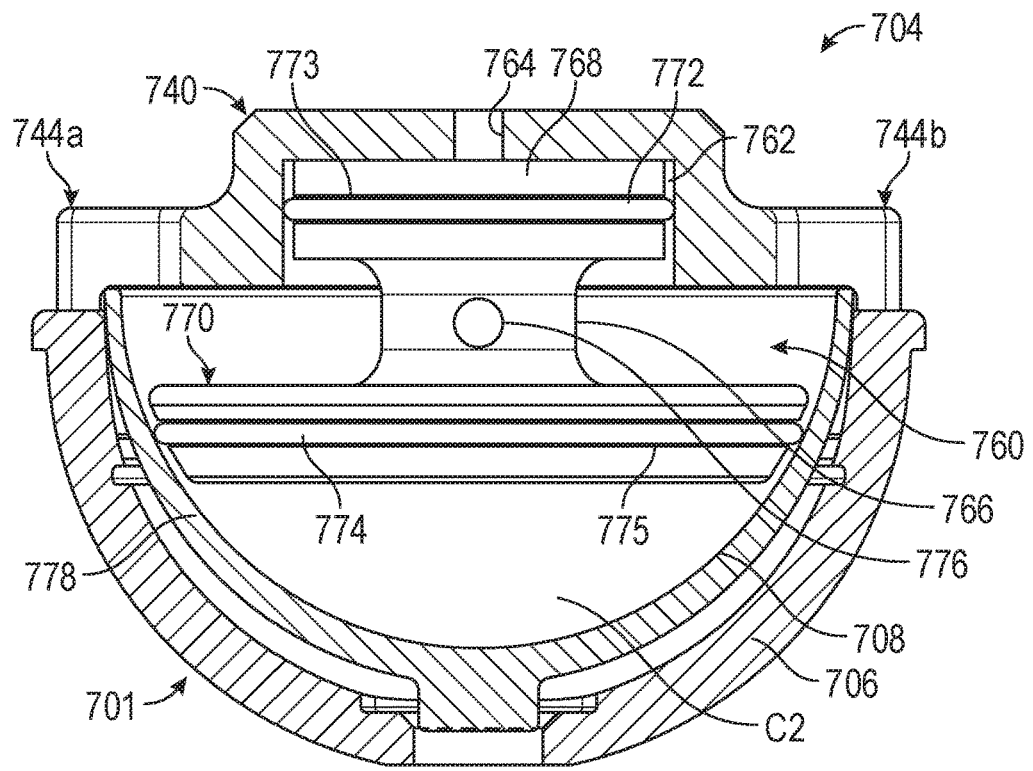
FIG. 8B illustrates a cross-sectional view of a portion of a tool assembly in a second condition, in accordance with at least one example of this disclosure.

FIG. 8A illustrates a cross-sectional view across indicators 8-8 of FIG. 7 of a portion of the tool assembly 700 in a first condition, in accordance with at least one example of this disclosure. FIG. 8B illustrates a cross-sectional view across indicators 8-8 of FIG. 7 of a portion of the tool assembly 700 in a second condition, in accordance with at least one example of this disclosure. FIGS. 8A and 8B are discussed below concurrently.

The tool assembly 700 can include the faceplate 704, which can include the body 740, arms 744a-744d, and a plunger 760. The implant 701 can include the outer shell 706 and the liner 708. The outer shell 706 can include notches 719. The body 740 can include a piston bore 762 and a conduit port 764. The plunger 760 can include a body 766, a proximal piston 768, a distal piston 770, a proximal gasket 772 (in a proximal groove 773), a distal gasket 774 (in a distal groove 775), and a body port 776. The liner 708 can include an inner wall 778. Also shown in FIGS. 8A and 8B are cavities C1 and C2 and orientation indicators Proximal and Distal.

The piston bore 762 of the body 740 can be a bore extending proximally into the body and configured to receive the proximal piston 768 therein. The conduit port 764 can be connected to the piston bore 762 such that the piston bore 762 is in fluid communication with the suction conduit 715 (of FIG. 7).

The body 766 of the plunger 760 can be a rigid or semi-rigid member connected to the proximal piston 768 and the distal piston 770 to form the plunger 760. In some examples, the body 766 can have a diameter smaller than a diameter of the proximal piston 768 and the distal piston 770, which can help reduce weight and cost of the plunger 760.

The proximal piston 768 can be connected to a proximal portion of the body 768 and can be sized to move in and out of the piston bore 762. The proximal piston 768 can have a shape substantially complimentary to the piston bore 762. The proximal piston 768 can include the proximal groove 773, which can be a circumferential groove extending around a radially outer axial surface of the proximal piston 768. The proximal groove 773 can be sized to receive the proximal gasket 772 such that the proximal piston 768 and the proximal gasket 772 can form a seal with the piston bore 768 while allowing proximal-to-distal (and reverse) movement of the proximal piston 768 with respect to the body 740.

The distal piston 770 can be connected to a distal portion of the body 768 and can be sized to move with respect to the implant 701. The distal piston 770 can include the distal groove 775, which can be a circumferential groove extending around a radially outer axial surface of the distal piston 770. The distal groove 775 can be sized to receive the distal gasket 774. The distal piston 770 can have a shape, together with the distal gasket 774, to engage the liner 708, such that the distal piston 770 and the distal gasket 774 can form a seal with the inner wall 778 of the liner.

In operation of some examples, the faceplate 704 can be inserted into an opening and can engage the outer shell 706, as discussed with respect to FIG. 7, and the tamp 707 (of FIG. 7) can be inserted into one of the notches 719 (of FIG. 7). Either before or after securing the faceplate 704 to the shell, the conduit 715 can be connected to the body 740 and the conduit 717 can be connected to the body 768 of the plunger 760. Suction can be applied through the suction conduits 715 and 717 (shown in FIG. 7). The suction conduit 717 can apply a suction (or negative pressure) to the body port 776 of the body 768 of the plunger 760. Because the distal piston 770 and the distal gasket 774 can form a seal with the inner wall 778 of the liner, the negative pressure applied through the body port 776 to the distal side of the distal plunger 770 can create a negatively pressurized volume in the cavity C2 between the distal plunger 770 and the inner wall 778 of the liner 708. The negative pressure of the cavity C2 can create a connection between the distal plunger 770 and the inner wall 778, causing the liner 708 to move together with the distal plunger 770.

Similarly, the suction conduit 715 can apply a suction (or negative pressure) to the piston bore 762 via the conduit port 764 of the body 740. Because the proximal piston 768 and the proximal gasket 772 can form a seal with the piston bore 768, the negative pressure within the cavity C1 between the piston bore and the proximal piston 768 can apply a distal-to-proximal force on the proximal piston 768, which can apply a similar (distal-to-proximal) force on the distal piston 770 and the liner 708.

The impactor 707 can then be impacted to transmit a force to the outer shell 706 where vibration of the outer shell 706 can cause the inner liner 708 to separate from the outer shell 706. Because the proximal piston 768 can move within the piston bore 768 and because the distal piston 770 is connected to the inner wall 778 via suction pressure, once the liner 708 separates from the shell 706, the distal-to-proximal force applied to the piston 760 and the liner 708 can cause the piston 760 and the liner 708 to move proximally with respect to the outer shell 706 after, indicating to a physician or surgeon that no further impacts are necessary and that the liner 708 is ready to be extracted.

Figure 9:
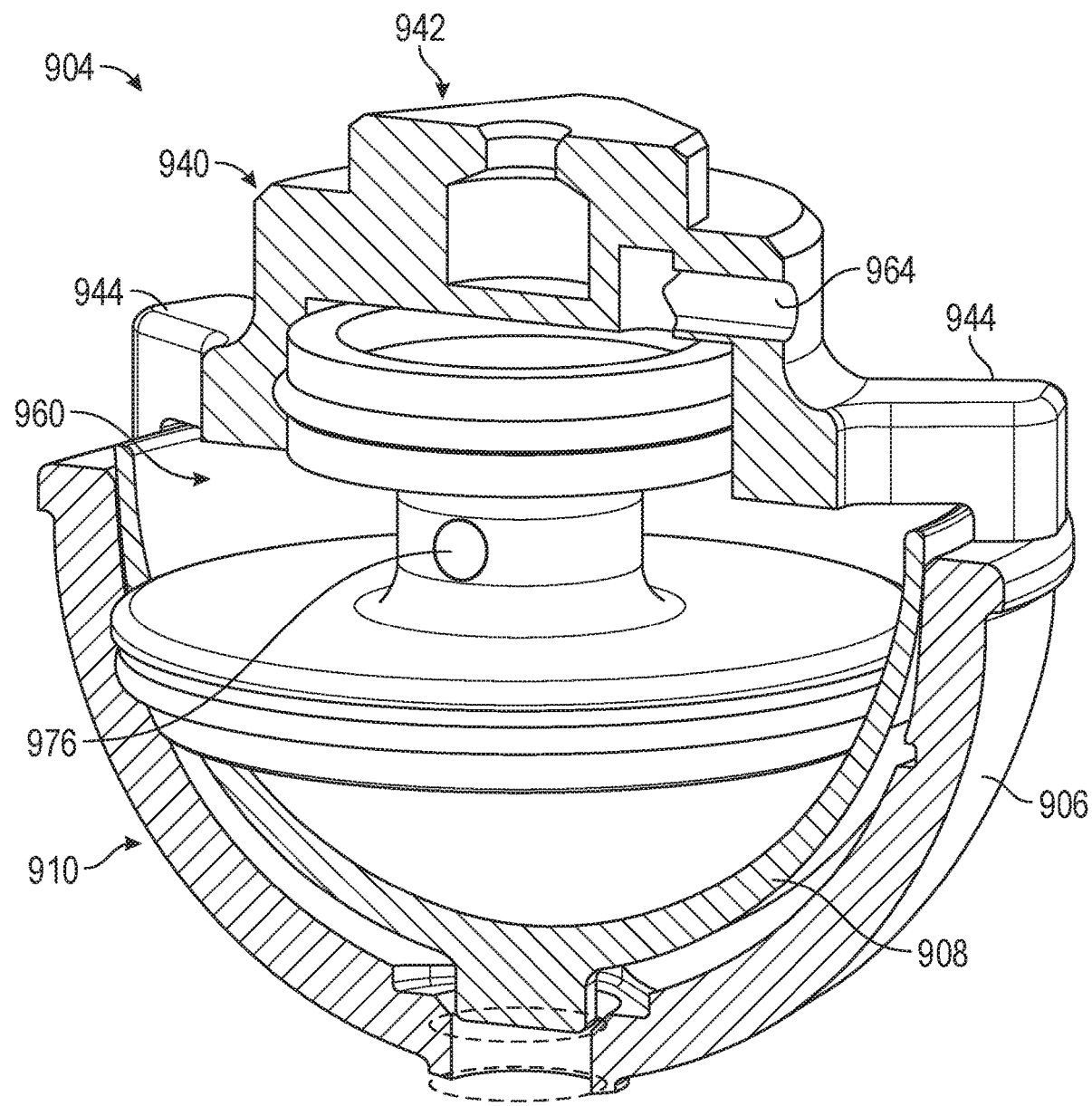
FIG. 9 illustrates a cross-sectional view of a portion of a tool assembly in accordance with at least one example of this disclosure.

FIG. 9 illustrates a cross-sectional view of a portion of a tool assembly 900, in accordance with at least one example of this disclosure. The tool assembly 900 can include a faceplate 904. The faceplate 904 can include a body 940, arms 944, and a plunger 960. The body 940 can include a boss 942 and a conduit port 964. The plunger 960 can include a body port 976. An implant 901 can include a shell 906 and a liner 908. Also shown in FIG. 9 are orientation indicators Proximal and Distal.

The tool assembly 900 can be similar to the tool assembly 700 except that the body 940 can include the boss 942 where the boss 942 can be configured to connect to a coupler of an impactor, such as the coupler 114 of the impactor 102 discussed above. The boss 942 can be substantially rectangular (or square or the like) and can be complimentary to a bore of the coupler for releasable mating of the coupler to the boss 942 to secure the faceplate 904 to the impactor. The tool assembly 900 can also differ in that the conduit port 964 can extend through a side of the body 940 to help avoid interfering with a connection between the boss 942 and the coupler. The plunger 960 can operate similarly to the plunger 760 discussed above.

Figure 10B:
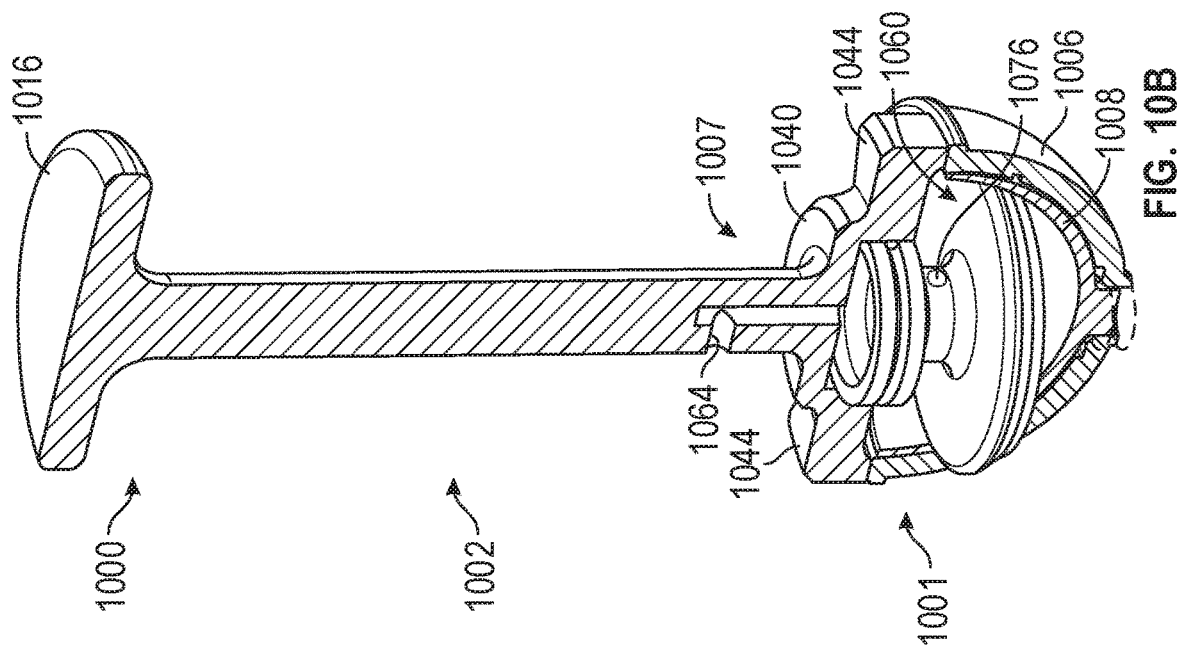
FIG. 10B illustrates a cross-sectional view of a portion of a tool assembly, in accordance with at least one example of this disclosure.
Figure 10A:
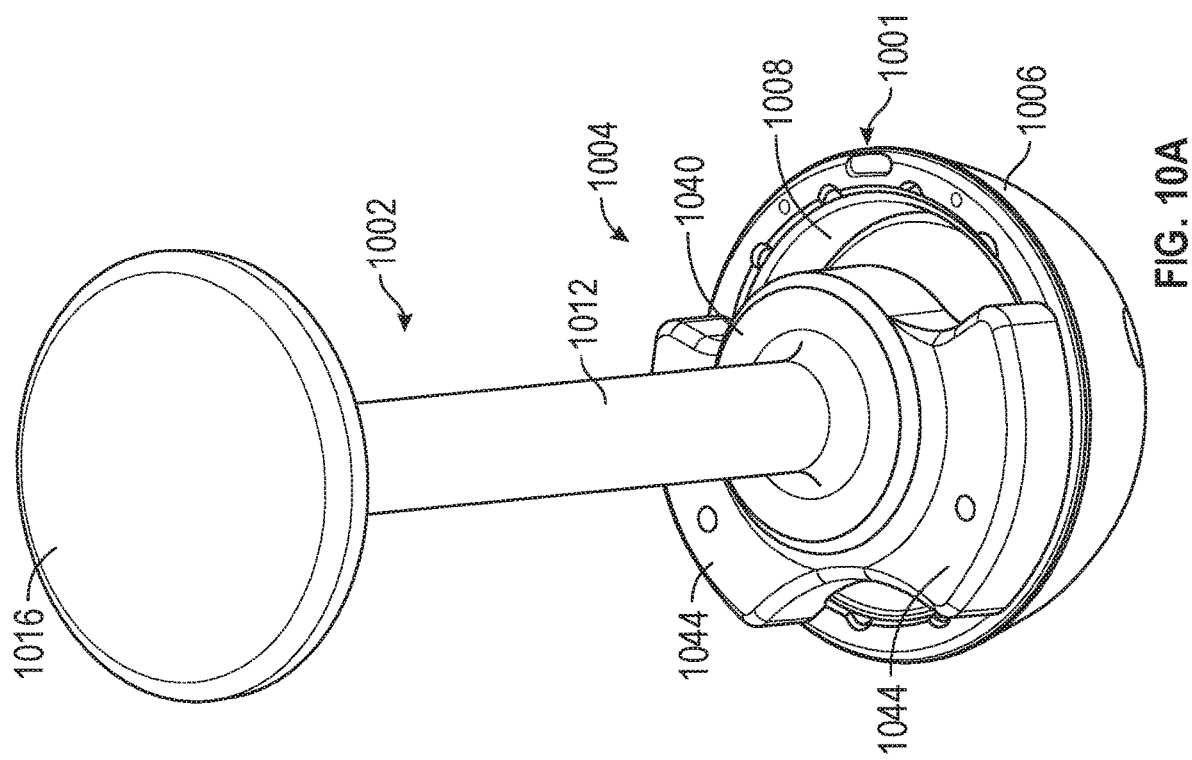
FIG. 10A illustrates a cross-sectional view of a portion of a tool assembly, in accordance with at least one example of this disclosure.

FIG. 10A illustrates a cross-sectional view of a portion of a tool assembly 1000, in accordance with at least one example of this disclosure. FIG. 10B illustrates a cross-sectional view of a portion of the tool assembly 1000, in accordance with at least one example of this disclosure. FIGS. 10A and 10B are discussed below concurrently.

The tool assembly 1000 can include an impactor 1002 and a faceplate 1004. An implant 1001 can include a shell 1006 and a liner 1008. The impactor 1002 can include a shaft 1012 and a strike plate 1016. The shaft 1012 can include a conduit port 1064. The faceplate 1004 can include a body 1040, arms 1044, and a plunger 1060. The plunger 1060 can include a body port 1076. Also shown in FIGS. 10A and 10B are orientation indicators Proximal and Distal.

The tool assembly 1000 can be similar to the tool assembly 700 discussed above except that the impactor 1002 can be rigidly connected to the faceplate 1004, which can simplify manufacturing of the tool assembly 1000. Further, the shaft 1012 can include the conduit port 1064, which can extend through the shaft 1012 and through the faceplate 1004 to reach a proximal side of the plunger 1060. The plunger 1060 can operate similarly to the plunger 760 discussed above.

Figure 11:
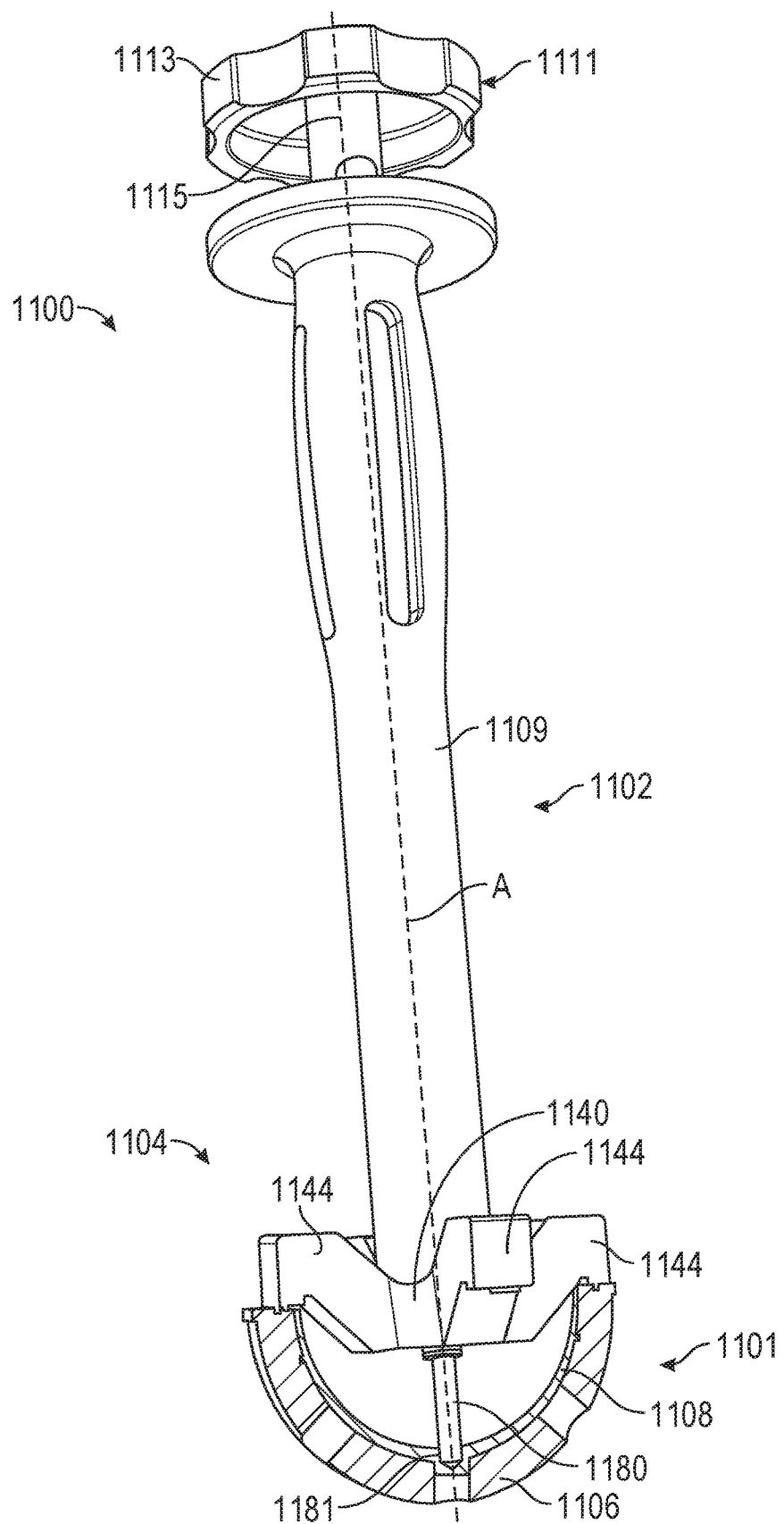
FIG. 11 illustrates an isometric view and a partial cross-sectional view of a tool assembly, in accordance with at least one example of this disclosure.

FIG. 11 illustrates an isometric view and a partial cross-sectional view of a tool assembly 1100, in accordance with at least one example of this disclosure. The tool assembly 1100 can include a removal tool 1102 and a faceplate 1104. An implant 1101 can include a shell 1106 and a liner 1108. The removal tool 1102 can include a sleeve 1109, a handle 1111, and a drill bit 1180. The faceplate 1104 can include a body 1140 and arms 1144. Also shown in FIG. 11 are axis A and orientation indicators Proximal and Distal.

The sleeve 1109 can extend along the axis A and can be substantially hollow such that the sleeve 1109 can receive a shaft 1115 of the handle 1111 therethrough. The shaft 1115 can be releasably couplable to the drill bit 1180 such that the drill bit 1180 can extend through the sleeve 1109 along with the shaft 1115. A knob 1113 can be secured to a proximal portion of a shaft 1115 of the handle 1111.

The arms 1144 can extend radially outward from the body 1140 of the faceplate and can be configured to engage the shell 1106. The body 1140 can be couplable to the sleeve 1109, such as through a threaded connection.

In other embodiments, the knob 1113 can be omitted and the shaft 1115 of the handle 1111 can be connected to a driver for driving rotation of the drill bit 1180. In yet other examples, the knob 1113 and the shaft 1115 can be configured to couple to a driver, such as an electric or pneumatic drill.

Further details and operation of the tool assembly 1100 are discussed below with respect to FIG. 13 (with further reference to FIGS. 11 and 12).

Figure 12:
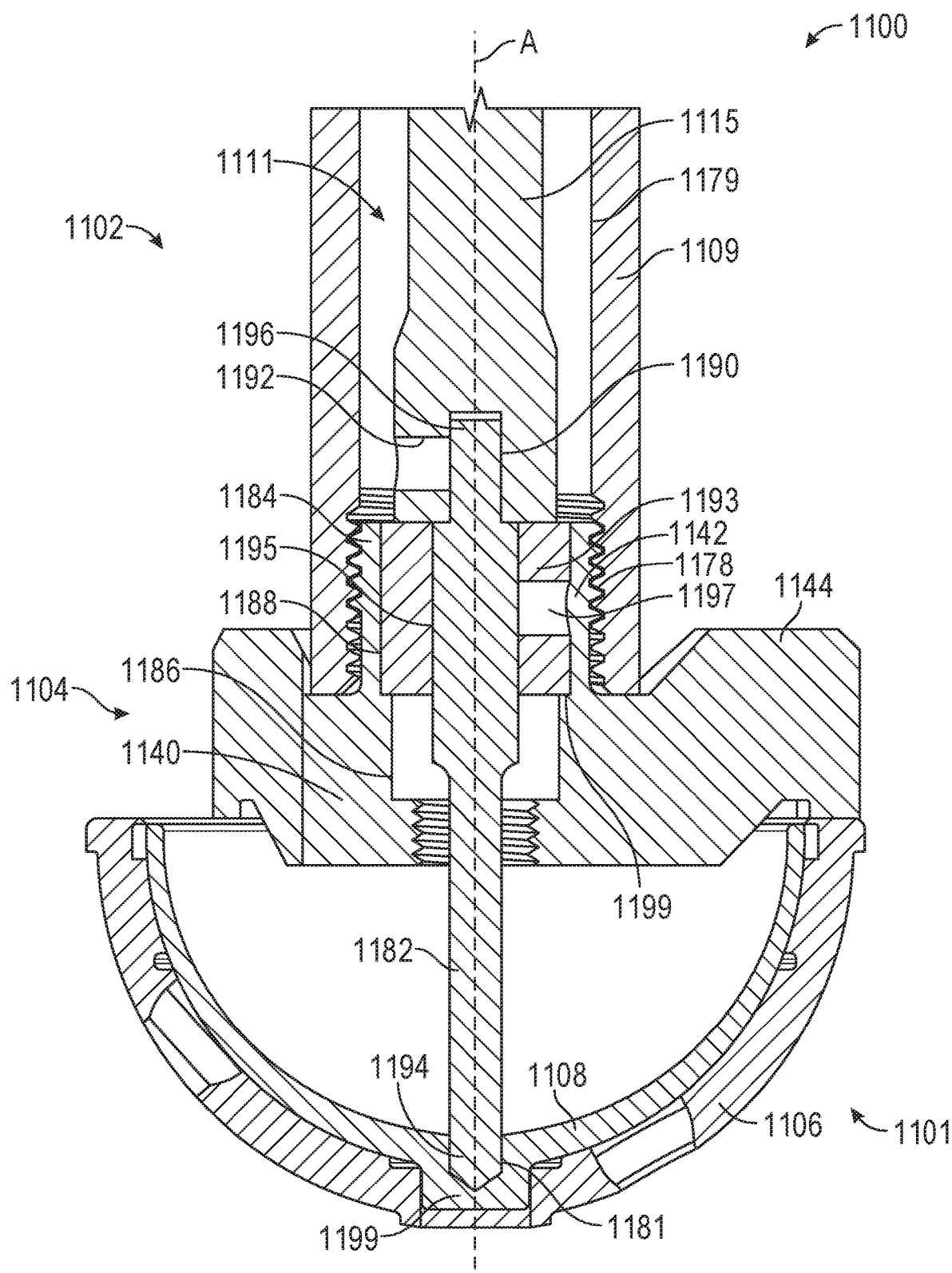
FIG. 12 illustrates a cross-sectional view of a tool assembly, in accordance with at least one example of this disclosure.

FIG. 12 illustrates a cross-sectional view of the tool assembly 1100, in accordance with at least one example of this disclosure. The tool assembly 1100 can be consistent with the tool assembly 1100 discussed above with respect to FIG. 11; further details are discussed with respect to FIG. 12.

For example, FIG. 12 shows that the faceplate 1104 can include a boss 1142 that can have a threaded portion 1184, a central bore 1186, and a bushing bore 1188. FIG. 12 further shows that the sleeve 1109 can include a central bore 1179 and a threaded portion 1188. Further, the handle 1111 can include the shaft 1115, a coupling bore 1190, and a set screw bore 1192. FIG. 12 further shows that the tool assembly 1100 can include a tap 1182 and a bushing 1193. The tap 1182 can include a tip 1194 and a tang 1196. The bushing 1193 can include a shank bore 1195 and a set screw bore 1197. Also shown in FIG. 12 are axis A and orientation indicators Proximal and Distal.

The boss 1142 can extend proximally from the body 1140 and can include the threaded portion 1184, which can be radially outer threads of the boss 1142. The threaded portion 1184 can be insertable into the sleeve 1109 and can be threadably securable to the threaded portion 1188 of the sleeve 1109 to secure the faceplate 1104 to the sleeve 1109. The central bore 1186 can extend through the body 1140 of the faceplate 1104 (and the boss 1142) substantially coaxially with the axis A. The bushing bore 1188 can extend into the boss 1142 from a proximal portion of the boss 1142. The busing bore 1188 can be sized to receive the busing 1193 therein.

The bushing 1193 can be connected to a distal portion of the shaft 1115 and can be configured to be a depth stop or depth limiter for the tap 1182. The tap 1182 can be a tool configured to tap threads into a bore, such as by using the tip 1194. The tang 1196 can be releasably couplable to the coupling bore 1190 where the set screw bore 1192 can receive a set screw therein to secure the tang 1196 to the coupling bore 1190 of the shaft 1115. Also, the set screw bore 1197 of the bushing can be used to releasably secure the bushing 1193 to the tap 1182.

Figure 13:
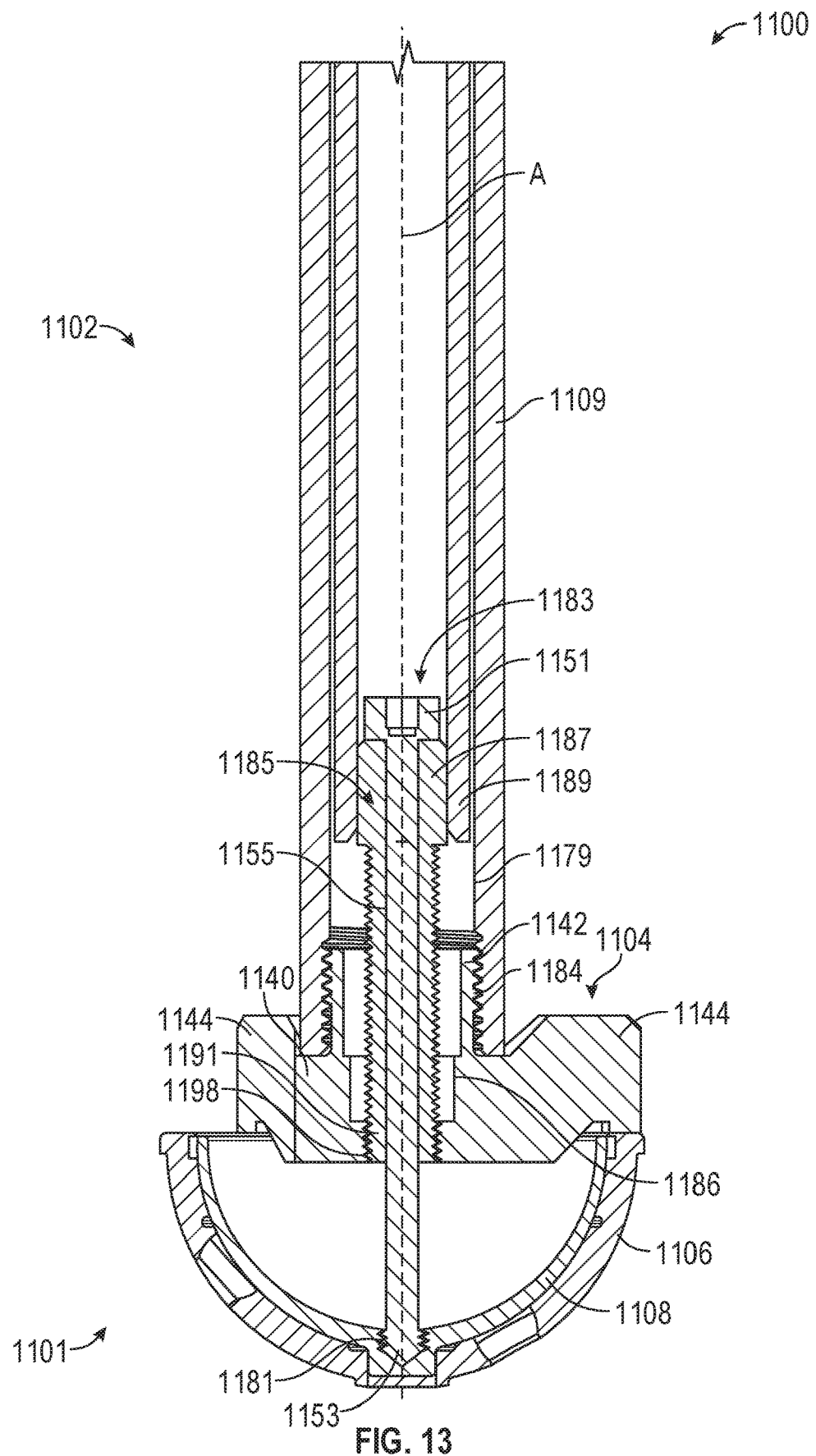
FIG. 13 illustrates a cross-sectional view of a tool assembly, in accordance with at least one example of this disclosure.

FIG. 13 illustrates a cross-sectional view of the tool assembly 1100, in accordance with at least one example of this disclosure. The tool assembly 1100 can be consistent with the tool assembly 1100 discussed above with respect to FIGS. 11 and 12; further details are discussed with respect to FIG. 13.

For example, FIG. 13 shows that the tool assembly 100 can include a handle 1185, which can include an inner shaft 1187 and an outer shaft 1189. The inner shaft 1187 can include a threaded portion 1191 and a bolt bore 1155. FIG. 13 also shows a bolt 1183, which can include a head 1151 and a threaded portion 1153. FIG. 13 also shows that the central bore 1186 of the body 1140 can include a distal threaded portion 1198. Also shown in FIG. 12 are axis A and orientation indicators Proximal and Distal.

The handle 1185 can be a tool insertable into the sleeve 1109 to separate the liner 1108 from the shell 1106. The outer shaft 1189 can have a diameter similar to the central bore 1179 of the sleeve 1109 to limit non-rotational and non-axial movement of the handle 1185 within the sleeve with respect to the axis A. The outer shaft 1189 can connect to a knob (similar to the knob 1113) and/or a driver and a proximal portion of the shaft 1189. The threaded portion 1191 of the inner shaft 1187 can threadably couple to the threaded portion 1198 of the faceplate 1104 to secure the handle 1185 of the faceplate 1104.

The bolt 1183 can be securable to the liner 1108 for separation of the liner 1108 from the shell 1106. The head 1151 can be similar to a head of a bolt and can be sized to engage a proximal radial surface of the inner shaft 1187 of the handle 1185. The threaded portion 1153 can be sized and shaped to threadably engage the tapped bore 1181 to secure the bolt 1183 to the liner 1108. The bolt 1183 can be sized to extend through the bolt bore 1155 of the inner shaft 1187 and can be rotatable therein (in non-threaded engagement) and translatable with respect thereto.

In operation, when it is desired to remove the liner 1108 from the shell 1106, an opening can be created in the patient and the faceplate 1104 can be positioned such that the arms 1144 contact the outer shell 1106. The sleeve 1109 can then be secured to the faceplate 1104 and the drill bit 1180 and the shaft 1115 can be inserted through the sleeve 1109 to engage the liner 1108. The knob 113 can be rotated to rotate the shaft 1115 and the drill bit 1180 to create the bore 1181 in the sleeve. In some examples, a driver can be used to rotate the shaft 1115.

After a drilling operation has been performed, the drill bit (1180 of FIG. 11) can be disconnected from the shaft 1115 by loosening a set screw from engaging the drill bit 1180. The tap 1182 can then be secured to the shaft 1115 such as by using the set screw. In other examples, other coupling interfaces (such as a chuck or collar) can be used. The bushing 1193 can be secured to a shank of the tap 1182 such as by using a set screw within the bore 1197 to engage the tap 1182. (The bushing 1193 can also be used with the drill bit 1180). The shaft 1115 can then be inserted into the central bore 1179 of the sleeve 1109 until the tip 1194 of the tap engages the bore 1181. The knob 1113 can be rotated about the axis A to tap the bore 1181. A distal depth of the tip 1194 can be limited by contact between the bushing 1193 and a radial face 1199 formed by the central bore 1186 and the bushing bore 1188. Different sized bushings can be used adjust a tapping depth (or drilling depth—when using the drill bit 1180), allowing the removal tool 1102 to be used with implants of various sizes and shapes. When tapping of the bore 1181 is complete, the shaft 1115, bushing 1193 and tap 1182 can be removed from the sleeve 1109.

Following removal of the tap 1182, the handle 1185 can be inserted into the sleeve 1109 and the inner shaft 1187 can be threaded into the threaded portion 1191 of the central bore 1186 of the faceplate 1104 to secure the handle 1185 to the faceplate 1104. Then, the bolt 1183 can be inserted through the bolt bore 1155 of the inner shaft 1187 and the bolt 1183 can be threaded into the tapped bore 1181 to secure the bolt 1183 to the sleeve 1106. The handle 1185 can then be rotated to unthread the inner shaft 1187 from the threaded portion 1198 of the faceplate, which can cause the inner shaft 1187 to engage the head 1151 of the bolt 1183 to force the bolt 1183 proximally, forcing the liner 1108 proximally. A reaction force can be applied by the inner shaft 1187 to the faceplate 1104 and to the outer shell 1106 such that the proximal force applied to the liner 1108 and the distal force applied to the shell 1106 substantially cancel, which can help avoid disrupting a connection between the shell 1106 and an acetabulum of the patient. The liner 1108 can be forced proximally until it separates from the shell 1106 allowing the liner 1108 to be removed from the shell 1106.

Figure 14:
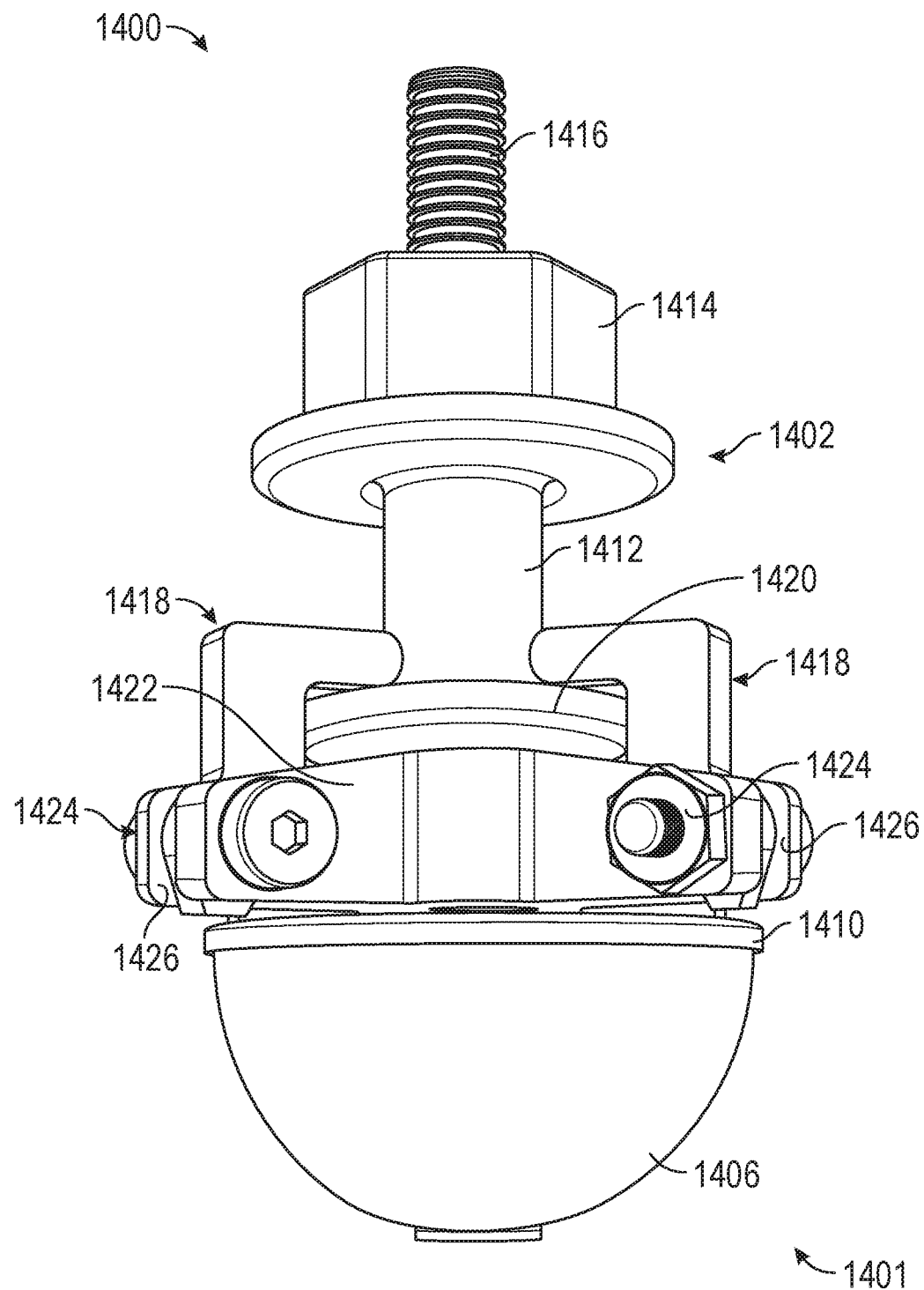
FIG. 14 illustrates an isometric view of a tool assembly, in accordance with at least one example of this disclosure.
Figure 15:
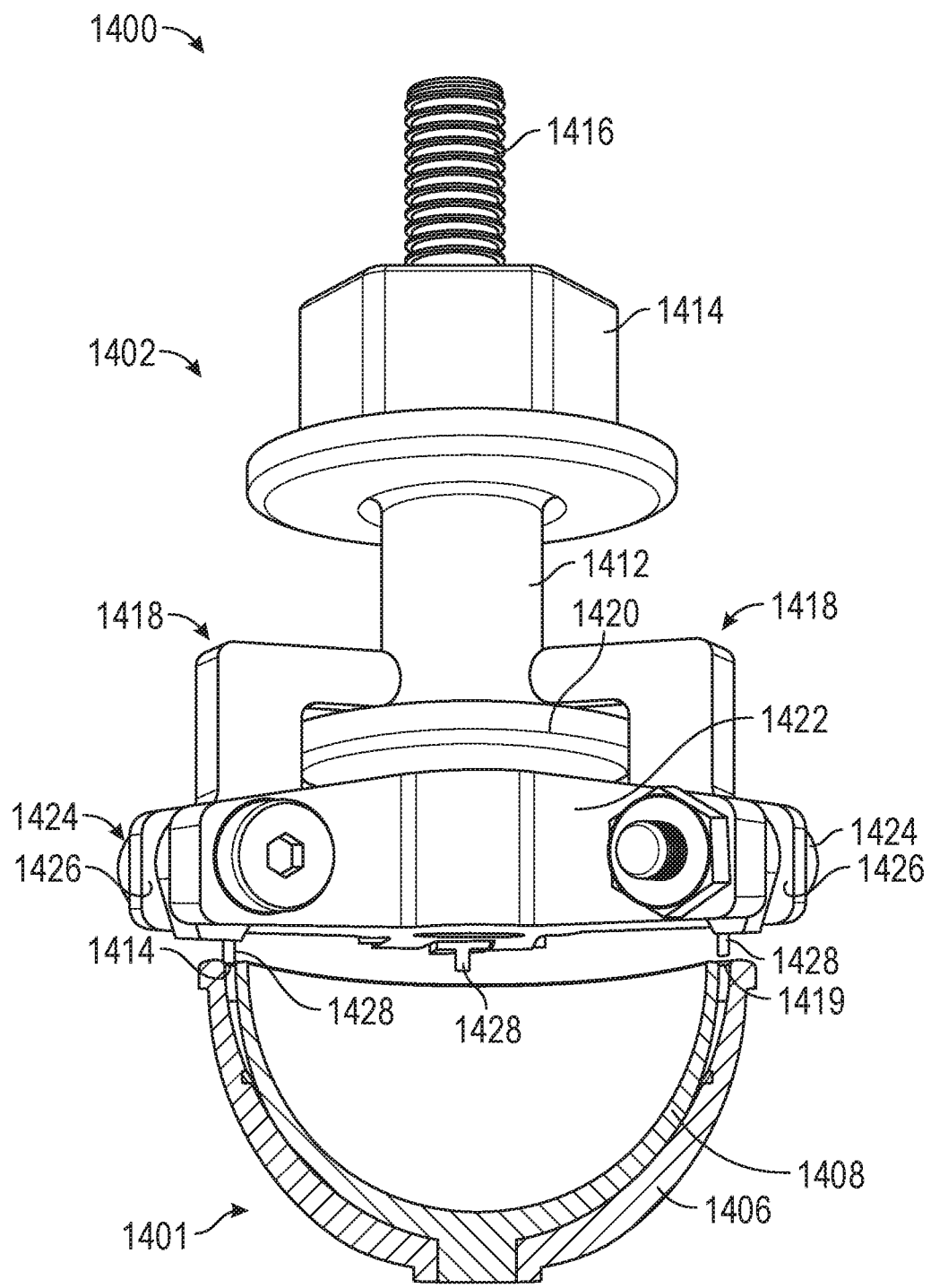
FIG. 15 illustrates an isometric view and a partial cross-sectional view of a tool assembly, in accordance with at least one example of this disclosure.

FIG. 14 illustrates an isometric view of a tool assembly 1400, in accordance with at least one example of this disclosure. FIG. 15 illustrates a isometric view and a partial cross-sectional view of the tool assembly 1400, in accordance with at least one example of this disclosure. FIGS. 14 and 15 are discussed below concurrently.

The tool assembly 1400 can include a removal tool 1402. An implant can include a shell 1406 and a liner 1408. The removal tool 1402 can include a body 1412, a nut 1414, a rod 1416, arms 1418, a flange 1420, a connector 1422, and fasteners 1424. The connectors 1422 can form gaps 1426. The arms 1418 can include projections 1428. The shell 1406 can include notches 1419. Also shown in FIGS. 14 and 15 are orientation indicators Proximal and Distal.

The nut 1414 can be connected to a proximal portion of the body 1412 and the flange 1420 can connect to a distal portion of the body 1412. The nut 1414 can be threadably engaged with the rod 1416, which can be a threaded rod secured to the connector 1422. The arms 1418 can be secured to the connector 1422 through fasteners 1424 such that the arms 1418 are pivotable about the fasteners 1424 with respect to the connector 1422. The projections 1428 can be sized and shaped for insertion into the notches 1419 between the shell 1406 and the liner 1408.

In operation, the nut 1414 can be rotated about the rod 1416 to cause the body 1412 and the flange 1420 to translate proximally. As the flange 1420 moves proximally, the arms pivot about the fasteners 1424, causing the projections 1428 to move radially inward to engage the liner 1408 and eventually deform the liner 1408 to separate the liner from the shell 1406.

Figure 16:
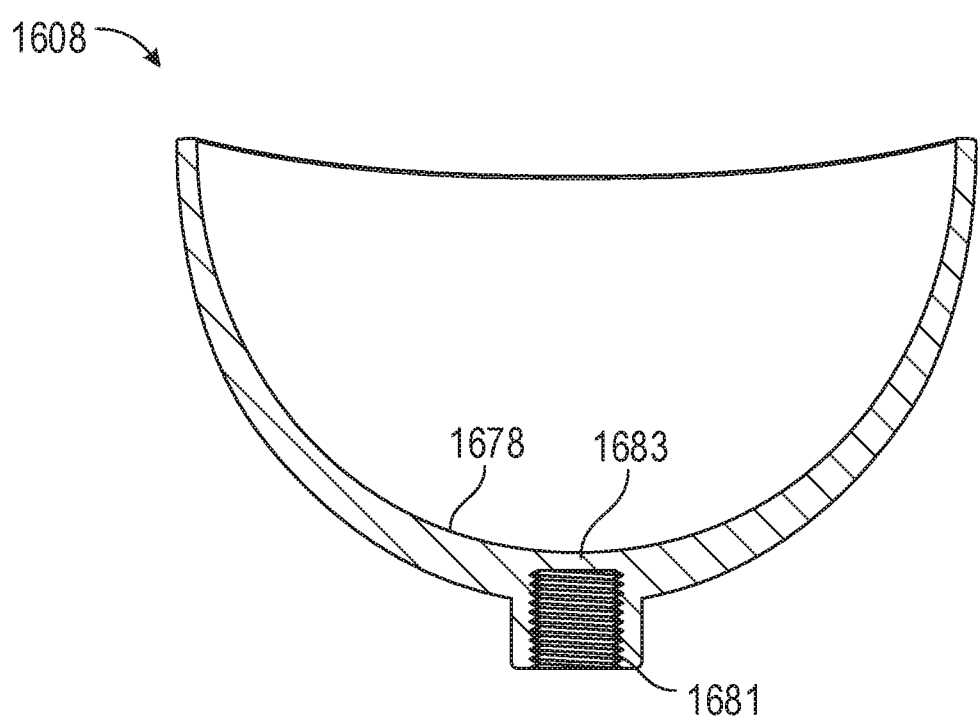
FIG. 16 illustrates a cross-sectional view of a portion of a tool assembly, in accordance with at least one example of this disclosure.

FIG. 16 illustrates a cross-sectional view of a liner 1608 of a tool assembly, in accordance with at least one example of this disclosure. The liner 1608 can include an inner wall 1678, a removal section 1683 and a tapped bore 1681. The tapped bore 1681 can be configured tot receive a bolt for removal of the liner 1608 from a shell (such as discussed with respect to FIGS. 11-13. The liner 1608 can include the removal portion 1683 which can be drilled through or punched out to expose the tapped bore 1681, which can reduce drilling and tapping operations performed on the liner 1608 for extraction of the liner 1608 from a shell.

Figure 17:
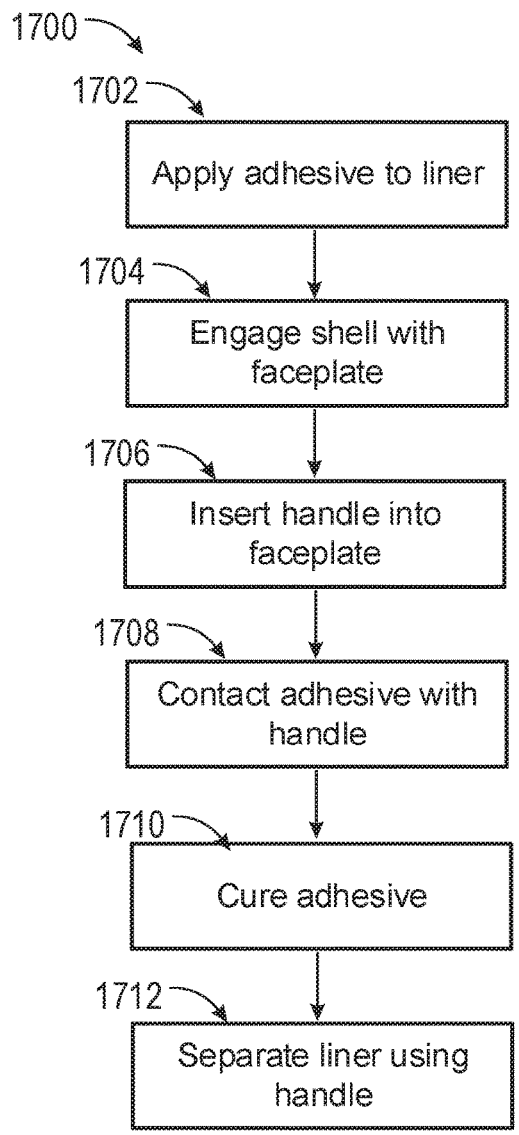
FIG. 17 a flow schematic of a method, in accordance with at least one example of this disclosure.

FIG. 17 a flow schematic of a method, in accordance with at least one example of this disclosure. The method 1700 can be a method of removing a liner from an outer shell of an implant using an adhesive and a removal tool. The steps or operations of the method 1700 are illustrated in a particular order for convenience and clarity; many of the discussed operations can be performed in a different sequence or in parallel without materially impacting other operations. The method 1700 as discussed includes operations performed by multiple different actors, devices, and/or systems. It is understood that subsets of the operations discussed in the method 1700 can be attributable to a single actor, device, or system could be considered a separate standalone process or method.

The method 1700 can be begin at step 1702 where an adhesive can be applied to an apex of the liner. At step 1704, a faceplate can be engaged with the shell. At step 1706, a handle can be inserted through a center of the faceplate. At step 1708, the distal end of the handle can contact the adhesive and at step 1710 the adhesive can be cured or allowed to set to secure the handle to the liner. At step 1712, the handle can be rotated to separate the liner from the shell of the prosthesis or implant. In some examples, the liner can be lavaged and dried prior to applying the adhesive to the liner.

For example, the liner 606 can be lavaged and dried. The faceplate 604 can be secured to the shell 606. Either before or after securing the faceplate, the adhesive 605 can be applied to a nadir or low point (apex from an inverted perspective) of the liner 606. The shaft 612 can be inserted into the bore 609 and secured to the faceplate 604 and can be positioned to contact the adhesive 605. The adhesive 605 can be cured or allowed to set to secure the shaft 612 of the removal tool 6 to the liner 606. The handle 613 of the removal tool 602 can be rotated to apply the torque T to the shaft 612, causing the faceplate to create the forces F1 applied to the shell 606 and causing the shaft 612 to apply the force F2 to the liner 606 through the adhesive 605. The force F2 can cause shaft 612 to separate the liner 606 from the shell 608 of the implant 601.

Figure 18:
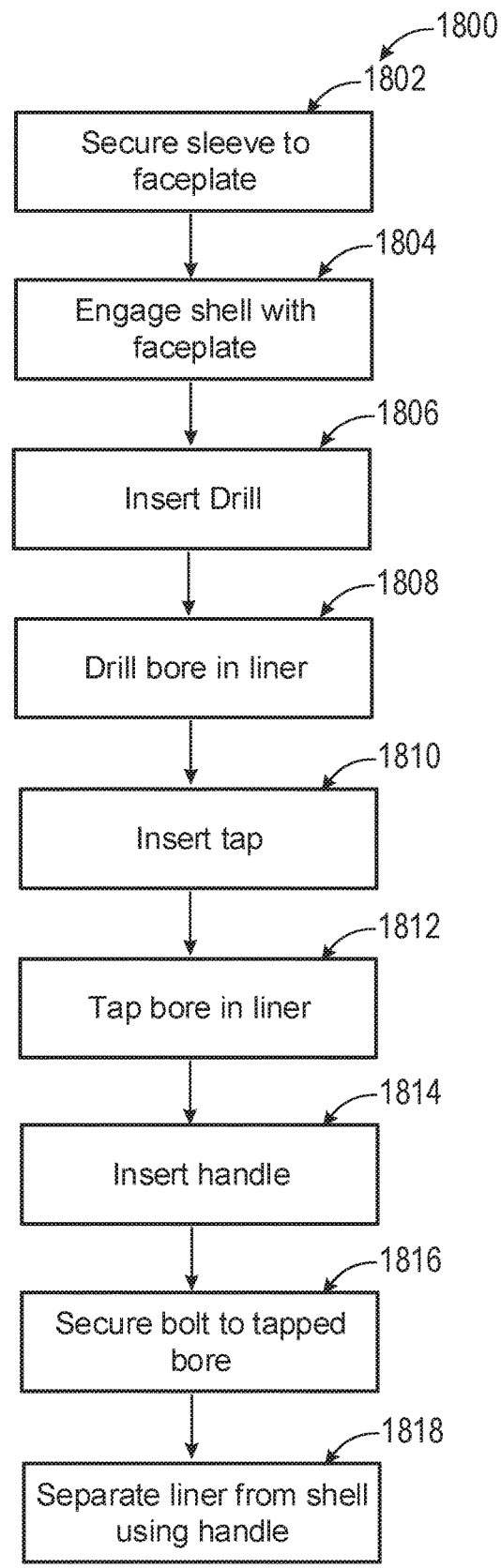
FIG. 18 a flow schematic of a method, in accordance with at least one example of this disclosure.

FIG. 18 a flow schematic of a method, in accordance with at least one example of this disclosure. The method 1800 can be a method of removing a liner from an outer shell of an implant using a removal tool. The method 1800 can be begin at step 1802 where a sleeve of a tool assembly can be secured to a faceplate of the tool assembly. For example, the sleeve 1109 can be secured to the faceplate 1104 (such as via the boss 1142). At step 1804, a faceplate can be engaged with the shell. For example, the faceplate 1804 can be engaged with the shell 1106.

At step 1806, a drill can be inserted through a central bore of the sleeve and through a central bore of the faceplate. For example, the drill bit 1180 can be inserted through the central bore 1179 of the sleeve 1109 and through the central bore 1186 of the faceplate. At step 1808, a bore can be drilled in the liner using the drill. For example, the bore 1181 can be drilled in the liner 1106 using the drill bit 1180.

At step 1810, a tap can be inserted through the central bore of the sleeve and through the central bore of the faceplate 1104. For example, the tap 1182 can be inserted through the central bore 1179 of the sleeve 1109 and through the central bore 1186 of the faceplate 1104. At step 1812, the bore in the liner can be tapped using the tap. For example, the bore 1181 can be tapped in the liner 1108 using the tap 1182. At step 1814, the handle 1185 can be inserted through the central bore 1179 of the sleeve 1109 and the handle 1185 can be secured to the central bore 1186 of the faceplate 1104.

At step 1816, a bolt can be inserted through the handle and secured to the tapped bore. For example, the bolt 1183 can be inserted through the handle 1185 and the bolt 1183 can be secured to the tapped bore 1181 of the liner 1108. At step 1818, the handle can be rotated to separate the liner from the shell of the prosthesis. For example, the handle 1185 can be rotated to separate the liner 1108 from the shell 1106.

NOTES AND EXAMPLES

The following, non-limiting examples, detail certain aspects of the present subject matter to solve the challenges and provide the benefits discussed herein, among others.

Example 1 is a tool assembly for extracting a liner from a prosthesis, the tool comprising: an impactor configured to receive and transmit a force, the impactor comprising: a handle extending along a longitudinal axis and configured to be impacted on a proximal portion of the handle; a shaft connected to a distal portion of the handle and extending distally therefrom along the longitudinal axis; and a coupler connected to a distal portion of the shaft, the coupler including a mating interface; and a faceplate configured to deliver the force from the impactor to the prosthesis, the faceplate comprising: a plurality of arms engageable with an outer shell of the prosthesis; and a boss releasably couplable to the mating interface to secure the faceplate to the impactor.

In Example 2, the subject matter of Example 1 optionally includes the handle further comprising: a balance bore sized to position a center of gravity of the impactor distal of the handle.

In Example 3, the subject matter of any one or more of Examples 1-2 optionally include the mating interface of the coupler further comprising: a magnet located in the coupler and configured to attract the boss to releasably secure the faceplate to the impactor.

In Example 4, the subject matter of Example 3 optionally includes the mating interface of the coupler further comprising: a coupler bore configured to receive the boss therein; and a magnet bore adjacent the coupler bore, the magnet secured within the magnet bore adjacent the coupler bore.

In Example 5, the subject matter of Example 4 optionally includes wherein the magnet is spaced from the coupler bore within the magnet bore such that the magnet magnetically attracts the boss to motivate the boss to enter the coupler bore and is spaced away from the boss when the boss is inserted fully into the coupler bore.

In Example 6, the subject matter of any one or more of Examples 1-5 optionally include the handle further comprising: a handle bore extending proximally into the handle from the distal portion of the handle, the shaft extending into the handle bore to secure the shaft to the handle.

In Example 7, the subject matter of Example 6 optionally includes the coupler further comprising: a shaft bore extending distally into the coupler from a proximal portion of the coupler, the shaft extending into the shaft bore to secure the shaft to the coupler.

In Example 8, the subject matter of Example 7 optionally includes wherein the handle is welded to the shaft near the shaft bore and wherein the coupler is welded to the shaft near the shaft bore.

In Example 9, the subject matter of Example 8 optionally includes wherein the handle includes a handle stop engaged with the shaft within the handle bore that is configured to transmit force to the shaft from the handle stop to reduce fatigue on the weld between the handle and the shaft, and wherein the shaft bore includes a coupler stop engaged with the shaft within the shaft bore that is configured to transmit force from the shaft to the coupler through the coupler stop to reduce fatigue on the weld between the coupler and the shaft.

In Example 10, the subject matter of any one or more of Examples 7-9 optionally include wherein the boss has a substantially rectangular prism shape and wherein the coupler bore has a substantially rectangular shape complimentary to the substantially rectangular prism shape of the boss.

In Example 11, the subject matter of any one or more of Examples 1-10 optionally include a strike plate secured to a proximal portion of the handle.

In Example 12, the subject matter of any one or more of Examples 1-11 optionally include the faceplate further comprising: a body supporting the boss and the plurality of arms, the plurality of arms extending radially outward from the body and the boss extending proximally from the body.

In Example 13, the subject matter of Example 12 optionally includes each of the plurality of arms further comprising: an extension extending distally from the arm and including a distal face configured to contact the outer shell of the prosthesis and configured to deliver the force thereto.

In Example 14, the subject matter of Example 13 optionally includes wherein each extension extends distally from the arms to allow the liner to move proximally of the distal face during extraction of the liner form the outer shell.

In Example 15, the subject matter of any one or more of Examples 13-14 optionally include each of the plurality of arms further comprising: a foot extending distally from the distal face, the foot insertable into a notch of the outer shell to limit rotation of the faceplate with respect to the outer shell when the foot is positioned within the notch.

Example 16 is a tool assembly for extracting a liner from a prosthesis, the tool comprising: an impactor configured to receive and transmit a force, the impactor comprising: a handle extending along a longitudinal axis thereof; a shaft connected to the handle and extending distally therefrom; and a coupler connected to a distal portion of the shaft, the coupler including a mating interface; and a faceplate configured to deliver the force from the impactor to the prosthesis, the faceplate couplable to the coupler, the faceplate comprising: a body; and a plurality of arms extending radially from the body, each of the arms engageable with an outer shell of the prosthesis.

In Example 17, the subject matter of Example 16 optionally includes the faceplate further comprising: a boss extending proximally from the body, the boss securable to the coupler to connect the faceplate to the impactor.

In Example 18, the subject matter of Example 17 optionally includes each of the plurality of arms further comprising: an extension extending distally from the arm and including a distal face configured to contact the outer shell of the prosthesis and to deliver the force thereto, each distal extension extending distally from the arms to allow the liner to move proximally of the distal face during extraction of the liner form the outer shell.

In Example 19, the subject matter of Example 18 optionally includes each of the plurality of arms further comprising: a foot extending distally from the distal face, the foot insertable into a notch of the outer shell to limit rotation of the faceplate with respect to the outer shell when the foot is positioned within the notch.

In Example 20, the subject matter of Example 19 optionally includes the mating interface of the coupler further comprising: a magnet located in the coupler and configured to attract the boss to releasably secure the faceplate to the impactor.

In Example 21, the subject matter of Example 20 optionally includes the mating interface of the coupler further comprising: a coupler bore configured to receive the boss therein; and a magnet bore adjacent the coupler bore, the magnet secured within the magnet bore adjacent the coupler bore, wherein the magnet is spaced from the coupler bore within the magnet bore such that the magnet magnetically attracts the boss to motivate the boss to enter the coupler bore and is spaced away from the boss when the boss is inserted fully into the coupler bore.

In Example 22, the subject matter of any one or more of Examples 16-21 optionally include a collar connected to the shaft and translatable thereon; and a stem extending proximally from the body, the stem insertable into the collar to secure the shaft to the faceplate, and the collar translatable to release the faceplate from the shaft.

In Example 23, the subject matter of any one or more of Examples 16-22 optionally include wherein the shaft is curved with respect to the longitudinal axis.

Example 24 is a method of separating a liner and a shell of a prosthesis, the method comprising: applying an adhesive to an apex of the liner; engaging a faceplate with the shell; inserting a removal tool through a center of the faceplate; contacting the adhesive with a distal end of the removal tool; curing the adhesive to secure the removal tool to the liner; and rotating the removal tool to separate the liner from the shell of the prosthesis.

In Example 25, the subject matter of Example 24 optionally includes leveraging the liner and drying the liner prior to applying the adhesive to the liner.

Example 26 is a tool assembly for separating a liner from an outer shell of a prosthesis, the tool comprising: a faceplate configured to deliver a force from an impactor to the liner, the faceplate comprising: a plurality of arms engageable with an outer shell of the prosthesis; a piston bore extending proximally into the faceplate from a distal portion of the faceplate; and a first port connected to the piston bore and extending through the faceplate; and a plunger translatable with respect to the faceplate, the plunger comprising: a body; a proximal piston connected to a proximal portion of the body and extending radially outward, the proximal piston insertable into the piston bore to form a seal between the plunger and the piston bore; and a distal piston connected to a distal portion of the body and extending radially outward, the proximal piston insertable into the liner bore to form a seal between the plunger and the liner, the distal piston including a second port extending through the distal piston and the body.

In Example 27, the subject matter of Example 26 optionally includes an impactor connected to the faceplate.

In Example 28, the subject matter of any one or more of Examples 26-27 optionally include wherein suction applied to the first port can create low pressure in a first cavity defined at least partially by the proximal piston to bias the piston proximally and wherein suction applied to the second port can create low pressure in a second cavity defined at least in part by the distal piston and the liner to secure the piston to the liner.

Example 29 is a tool assembly for extracting a liner from a prosthesis, the tool comprising: a sleeve extending along a longitudinal axis, the sleeve comprising: a central bore extending therethrough; and a coupler located at a distal portion of the sleeve, the coupler including a mating interface; a faceplate comprising: a plurality of arms engageable with an outer shell of the prosthesis; and a connector releasably couplable to the mating interface to secure the sleeve to the faceplate; and a handle insertable into the sleeve to engage and extract the liner when the sleeve is secured to the faceplate and when the faceplate is secured to the prosthesis.

In Example 30, the subject matter of any one or more of Examples 26-29 optionally include a drill insertable through the sleeve and configured to drill a bore in the liner, the drill engageable with the faceplate to limit a drilling depth of the drill into the liner.

In Example 31, the subject matter of Example 30 optionally includes a tap insertable through the sleeve and configured to tap the bore in the liner.

In Example 32, the subject matter of Example 31 optionally includes a handle insertable through the sleeve and securable to the faceplate.

In Example 33, the subject matter of Example 32 optionally includes a bolt insertable through the sleeve and securable to the tapped bore in the liner to secure the handle to the liner.

In Example 34, the subject matter of Example 33 optionally includes wherein the handle is rotatable to rotate the liner with respect to the outer shell when the bolt is secured to the liner.

Example 35 is a method of separating a liner and a shell of a prosthesis, the method comprising: securing a sleeve of a tool assembly to a faceplate of the tool assembly; engaging a faceplate with the shell; inserting a drill through a central bore of the sleeve and through a central bore of the faceplate; drilling a bore in the liner using the drill; inserting a tap through the central bore of the sleeve and through the central bore of the faceplate; tapping the bore in the liner using the tap; inserting a handle through the central bore of the sleeve and securing the handle to the central bore of the faceplate; inserting a bolt through the handle and securing the bolt to the tapped bore; rotating the handle to separate the liner from the shell of the prosthesis.

In Example 36, the apparatuses or method of any one or any combination of Examples 1-35 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A tool assembly for extracting a liner from a prosthesis, the tool comprising:
   an impactor configured to receive and transmit a force, the impactor comprising:
      a handle extending along a longitudinal axis and configured to be impacted on a proximal portion of the handle, the handle including a handle bore extending proximally into the handle from a distal portion of the handle;
      a shaft connected to a distal portion of the handle and extending distally therefrom along the longitudinal axis, the shaft extending into the handle bore to secure the shaft to the handle; and
      a coupler connected to a distal portion of the shaft, the coupler including a mating interface; and
   a faceplate configured to deliver the force from the impactor to the prosthesis, the faceplate comprising:
      a plurality of arms engageable with an outer shell of the prosthesis; and
      a boss releasably couplable to the mating interface to secure the faceplate to the impactor.

2. The tool assembly of claim 1, the handle further comprising:
   a balance bore sized to position a center of gravity of the impactor distal of the handle.

3. The tool assembly of claim 1, the mating interface of the coupler further comprising:
   a magnet located in the coupler and configured to attract the boss to releasably secure the faceplate to the impactor.

4. The tool assembly of claim 3, the mating interface of the coupler further comprising:
   a coupler bore configured to receive the boss therein; and a magnet bore adjacent the coupler bore, the magnet secured within the magnet bore adjacent the coupler bore.

5. The tool assembly of claim 4, wherein the magnet is spaced from the coupler bore within the magnet bore such that the magnet magnetically attracts the boss to motivate the boss to enter the coupler bore and is spaced away from the boss when the boss is inserted fully into the coupler bore.

6. The tool assembly of claim 1, the coupler further comprising:
a shaft bore extending distally into the coupler from a proximal portion of the coupler, the shaft extending into the shaft bore to secure the shaft to the coupler.

7. The tool assembly of claim 6 wherein the handle is welded to the shaft near the handle bore and wherein the coupler is welded to the shaft near the shaft bore.

8. The tool assembly of claim 7 wherein the handle includes a handle stop engaged with the shaft within the handle bore that is configured to transmit force to the shaft from the handle stop to reduce fatigue on the weld between the handle and the shaft, and wherein the shaft bore includes a coupler stop engaged with the shaft within the shaft bore that is configured to transmit force from the shaft to the coupler through the coupler stop to reduce fatigue on the weld between the coupler and the shaft.

9. The tool assembly of claim 6, wherein the boss has a substantially rectangular prism shape and wherein the coupler bore has a substantially rectangular shape complimentary to the substantially rectangular prism shape of the boss.

10. The tool assembly of claim 1, further comprising:
a strike plate secured to a proximal portion of the handle.

11. The tool assembly of claim 1, the faceplate further comprising:
a body supporting the boss and the plurality of arms, the plurality of arms extending radially outward from the body and the boss extending proximally from the body.

12. The tool assembly of claim 11, each of the plurality of arms further comprising:
an extension extending distally from the arm and including a distal face configured to contact the outer shell of the prosthesis and configured to deliver the force thereto.

13. The tool assembly of claim 12, wherein each extension extends distally from the arms to allow the liner to move proximally of the distal face during extraction of the liner form the outer shell.

14. The tool assembly of claim 12, each of the plurality of arms further comprising:
a foot extending distally from the distal face, the foot insertable into a notch of the outer shell to limit rotation of the faceplate with respect to the outer shell when the foot is positioned within the notch.

15. A tool assembly for extracting a liner from a prosthesis, the tool comprising:
an impactor configured to receive and transmit a force, the impactor comprising:
a handle extending along a longitudinal axis thereof;
a shaft connected to the handle and extending distally therefrom; and
a coupler connected to a distal portion of the shaft, the coupler including a mating interface; and
a faceplate configured to deliver the force from the impactor the prosthesis, the faceplate couplable to the coupler, the faceplate comprising:
a body; and
a plurality of arms extending radially from the body, each of the arms engageable with an outer shell of the prosthesis;
wherein the mating interface of the coupler includes a magnet located in the coupler configured to attract the boss to releasably secure the faceplate to the impactor.

16. The tool assembly of claim 15, the faceplate further comprising:
a boss extending proximally from the body, the boss securable to the coupler to connect the faceplate to the impactor.

17. The tool assembly of claim 16, each of the plurality of arms further comprising:
an extension extending distally from the arm and including a distal face configured to contact the outer shell of the prosthesis and to deliver the force thereto, each distal extension extending distally from the arms to allow the liner to move proximally of the distal face during extraction of the liner form the outer shell.

18. The tool assembly of claim 17, each of the plurality of arms further comprising:
a foot extending distally from the distal face, the foot insertable into a notch of the outer shell to limit rotation of the faceplate with respect to the outer shell when the foot is positioned within the notch.

19. A tool assembly for extracting a liner from a prosthesis, the tool comprising:
an impactor configured to receive and transmit a force, the impactor comprising:
a handle extending along a longitudinal axis and configured to be impacted on a proximal portion of the handle;
a shaft connected to a distal portion of the handle and extending distally therefrom along the longitudinal axis; and
a coupler connected to a distal portion of the shaft, the coupler including a mating interface; and
a faceplate configured to deliver the force from the impactor to the prosthesis, the faceplate comprising:
a plurality of arms engageable with an outer shell of the prosthesis; and
a boss releasably couplable to the mating interface to secure the faceplate to the impactor;
wherein the mating interface of the coupler includes a magnet located in the coupler configured to attract the boss to releasably secure the faceplate to the impactor.

20. The tool assembly of claim 19, the faceplate further comprising:
a body supporting the boss and the plurality of arms, the plurality of arms extending radially outward from the body and the boss extending proximally from the body.

* * * * *

UNITED STATES PATENT AND TRADEMARK OFFICE
CERTIFICATE OF CORRECTION

PATENT NO. : 11,452,620 B2
APPLICATION NO. : 16/448623
DATED : September 27, 2022
INVENTOR(S) : Furore et al.

Page 1 of 1

It is certified that error appears in the above-identified patent and that said Letters Patent is hereby corrected as shown below:

In the Claims

In Column 22, Line 4, in Claim 15, after "impactor", insert --to--

Signed and Sealed this
Third Day of January, 2023

*Katherine Kelly Vidal*

Katherine Kelly Vidal
*Director of the United States Patent and Trademark Office*